US012661215B2

(12) United States Patent
Guo et al.

(10) Patent No.: US 12,661,215 B2
(45) Date of Patent: Jun. 23, 2026

(54) VASCULAR SHUNT STENT AND VASCULAR STENT

(71) Applicant: HANGZHOU ENDONOM MEDTECH CO., LTD, Hangzhou (CN)

(72) Inventors: Wei Guo, Hangzhou (CN); Yongsheng Wang, Hangzhou (CN); Liman Shang, Hangzhou (CN)

(73) Assignee: Hangzhou EndoNom Medtech Co., Ltd, Hangzhou (CN)

( * ) Notice: Subject to any disclaimer, the term of this patent is extended or adjusted under 35 U.S.C. 154(b) by 837 days.

(21) Appl. No.: 17/981,434

(22) Filed: Nov. 6, 2022

(65) Prior Publication Data

US 2023/0056469 A1 Feb. 23, 2023

Related U.S. Application Data

(63) Continuation of application No. PCT/CN2021/090039, filed on Apr. 26, 2021.

(30) Foreign Application Priority Data

May 6, 2020 (CN) .......................... 202010376175.8
May 6, 2020 (CN) .......................... 202020727524.1

(51) Int. Cl.
*A61F 2/07* (2013.01)
*A61F 2/06* (2013.01)

(52) U.S. Cl.
CPC .......... *A61F 2/07* (2013.01); *A61F 2002/061* (2013.01)

(58) Field of Classification Search
CPC .................. A61F 2/07; A61F 2002/061; A61F 2220/0016
(Continued)

(56) References Cited

U.S. PATENT DOCUMENTS

2007/0038291 A1* 2/2007 Case ..................... A61F 2/2418
623/1.16
2014/0277369 A1 9/2014 Roeder et al.
(Continued)

FOREIGN PATENT DOCUMENTS

CN 105662511 A 6/2016
CN 105662649 A 6/2016
(Continued)

OTHER PUBLICATIONS

Translation of CN 209661880 (Year: 2019).*
Extended European Search Report Dated Apr. 24, 2024 for Corresponding European Application No. 21800784.7.

*Primary Examiner* — Brian E Pellegrino

(57) ABSTRACT

A vascular shunt stent includes a main body tube and at least one branch tube axially inserted into an inner lumen of the main body tube. The main body tube includes a tubular main membrane. At least one branch tube includes a tubular branch membrane, which is accommodated in an inner lumen of the main membrane. A first sealing film is arranged between a distal end of the main membrane and a distal end of the branch membrane to separate the inner lumen of the main membrane into a main opening and at least one first sub-opening, the first sub-opening is in sealed connection with the distal end of the branch membrane. An included angle between a plane defined by the first sub-opening is not parallel with a plane defined by the main opening.

16 Claims, 14 Drawing Sheets

(58) Field of Classification Search
USPC .......................................................... 623/1.35
See application file for complete search history.

(56)                       References Cited

U.S. PATENT DOCUMENTS

| 2015/0209163 | A1 | 7/2015 | Kelly |
| 2020/0085560 | A1 | 3/2020 | Parodi et al. |
| 2020/0315820 | A1 | 10/2020 | Guo et al. |

FOREIGN PATENT DOCUMENTS

| CN | 107771066 A | * | 3/2018 | ............... A61F 2/07 |
| CN | 108261250 A | | 7/2018 | |
| CN | 109833116 A | | 6/2019 | |
| CN | 209405013 U | | 9/2019 | |
| CN | 209661880 U | * | 11/2019 | ............... A61F 2/82 |
| WO | WO-2010024879 A1 | * | 3/2010 | ............. A61F 2/856 |
| WO | 2018/031632 A1 | | 2/2018 | |

* cited by examiner

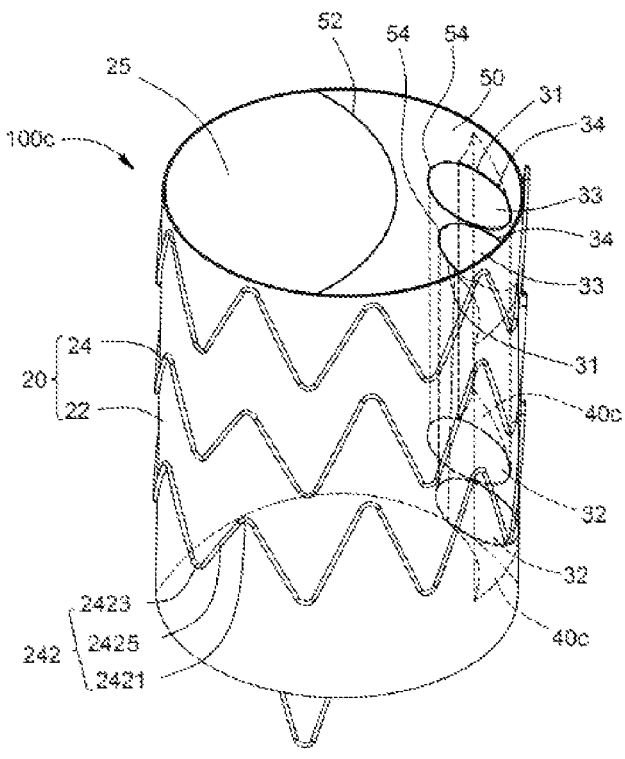
FIG. 12
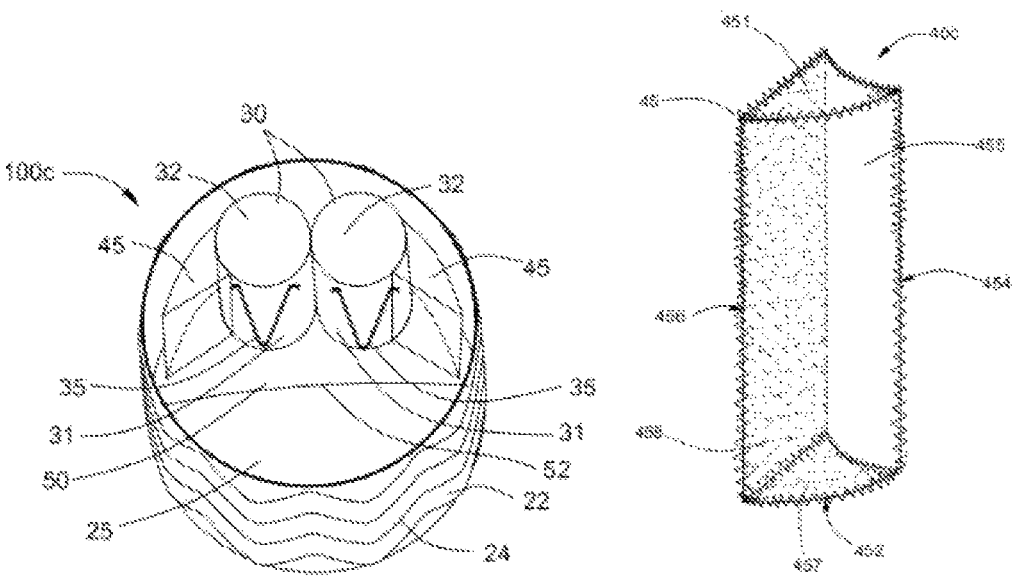
FIG. 13            FIG. 14

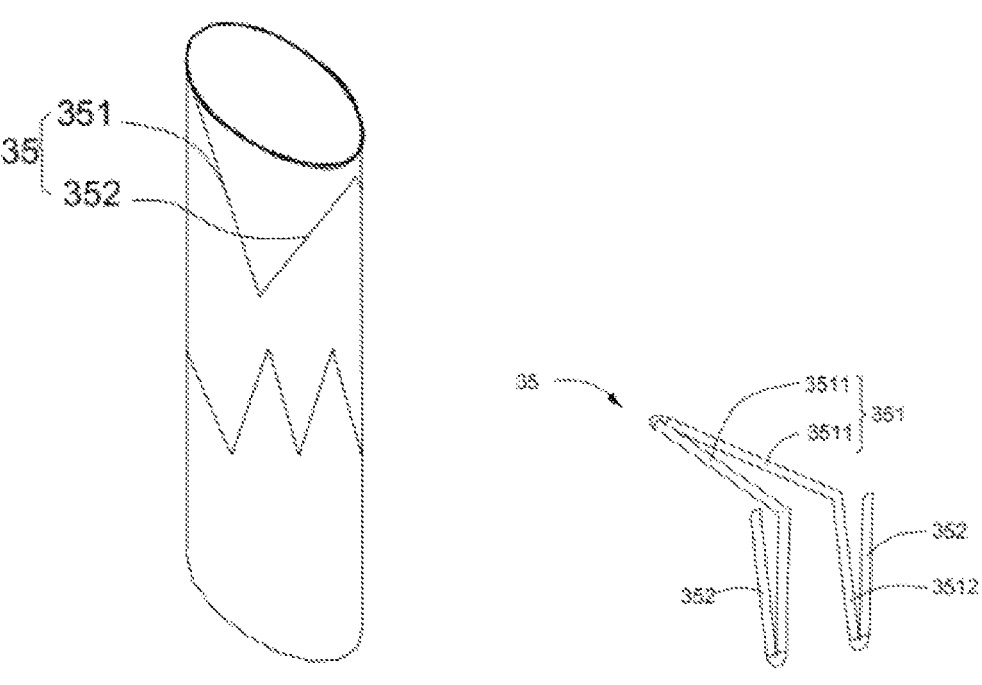
FIG. 27                                    FIG. 28
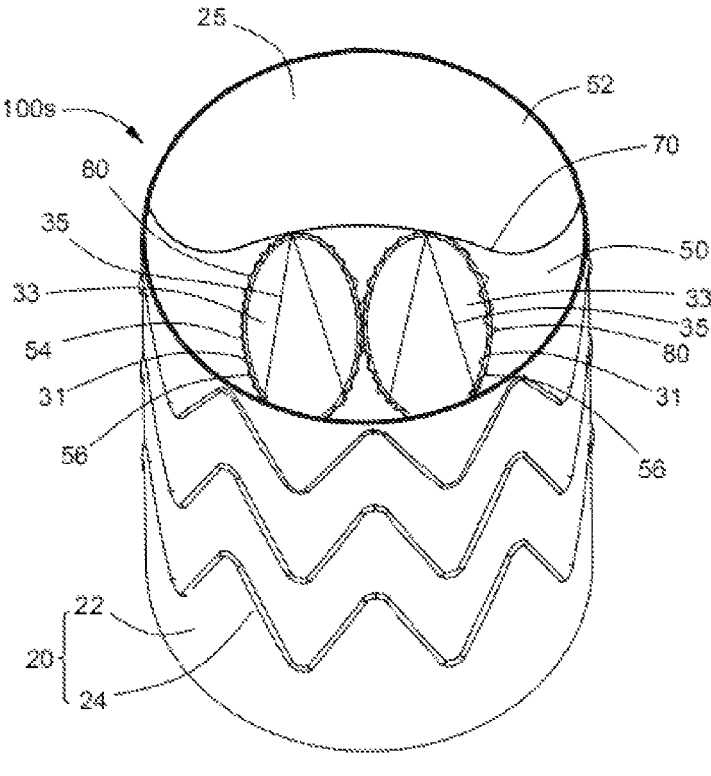
FIG. 29

VASCULAR SHUNT STENT AND VASCULAR STENT

CROSS REFERENCE OF RELATED APPLICATIONS

The present application is a Continuation Application of PCT Application No. PCT/CN2021/090039, filed on Apr. 26, 2021, which claims the priority of Chinese Patent Application No. 202010376175.8, filed on May 6, 2020, and the priority of Chinese Utility Model Application No. 202020727524.1, filed on May 6, 2020, the entire contents of which are hereby incorporated by reference.

TECHNICAL FIELD

The present disclosure relates to the technical field of implantable blood vessels, and particularly to a vascular shunt stent and a vascular stent provided with the vascular shunt stent.

BACKGROUND

Aortic aneurysm refers to local or diffusive abnormal expansion of the aortic wall, which causes symptoms due to compression of adjacent organs, and the major hazard thereof is tumor rupture. It usually occurs in the ascending aortic arch, descending thoracic aorta, thoracoabdominal aorta, and abdominal aorta. Aortic aneurysms can be sorted into true aortic aneurysms and pseudo-aortic aneurysms by structure. The aortic aneurysm causes increased pressure on the inner side of the vessel, so it expands progressively. If it has been developed for a long time, the aortic aneurysm will eventually rupture, and the larger the aneurysm, the greater the possibility for rupture. According to statistics, without surgical treatment, 90% of patients suffering from thoracic aortic aneurysms will die within 5 years, and 75% of patients suffering from abdominal aortic aneurysms will die within 5 years.

Aortic dissection is another serious aortic disease. Aortic dissection refers to the damage of the media layer of the thoracic aorta, bleeding in the vessel wall, and blood entering a position between the media layer and the intimal layer of the vessel wall. Due to the impact of blood flow, once the aortic dissection is formed, the tear can be extended in the direction of blood flow, the dissection and the false lumen are enlarged, and the true lumen is compressed. Therefore, the dangers that may occur in patients suffering from aortic dissection include: (1) the threat of complete rupture of the blood vessel, wherein once the blood vessel is completely ruptured, the mortality rate is extremely high; (2) gradual enlargement of the dissection, compressing the true lumen, such that blood supplied at the distal end of the blood vessel is decreased. In most cases, aortic dissection is secondary to or coexisting with aortic aneurysm. The Oxford vessel disease study in the UK shows that the incidence of aortic dissection in natural populations is about 6/100,000 per year, and the incidence in males is higher than that in females, with a mean onset age of 63 years. The incidence of aortic dissection in China is much higher than that in European and American, and the age of onset is relatively young.

Aortic diseases may involve branch arteries. Once branch arteries are involved, it will be difficult to solve them through interventional methods. At present, endovascular treatment of aortic diseases has been carried out all over the world, that is, a minimally invasive method is employed, which involves implanting a graft, i.e., an arterial vascular stent into a lesioned artery through a vessel lumen to treat the arterial disease and improve blood supply, thereby achieving the purpose of treatment. The arterial vascular stent in the vessel lumen is composed of a tubular rigid wire stent and a polymer membrane fixed outside the tubular rigid wire stent. The tubular rigid wire stent is made by bending a resilient rigid wire in a Z shape to form a loop and then stitching or gluing multiple rings with the polymer membrane to form a covered stent. In use, the covered stent is compressed axially, then loaded into a delivery device, and delivered to the lesioned artery through the smaller femoral artery, the iliac artery, and the brachial artery by the delivery device, and then released. Due to the elastic force of the metal wire stent, the covered stent is automatically restored to a straight tube and tightly attached to the inner wall of the aorta, isolating the diseased part of the artery from the blood flow, thus achieving the purpose of treatment.

In the prior art, stents generally used relating to arterial branch therapy include chimney type stent, integrated stent with multiple branches, and fenestration type stent. However, these stents are limited by the structures thereof, and often bring inconvenience for inserting branch stents.

SUMMARY

In view of this, an objective of the present disclosure is to provide a vascular shunt stent bringing convenience for inserting branch tube stents, and a vascular stent provided with the vascular shunt stent.

In order to solve the above technical problems, the present disclosure provides a vascular shunt stent, which includes a main body tube and at least one branch tube axially inserted into an inner lumen of the main body tube. The main body tube includes a tubular main membrane, at least one branch tube includes a tubular branch membrane, and the branch membrane is accommodated in an inner lumen of the main membrane. A first sealing film is arranged between a distal end of the main membrane and a distal end of the branch membrane to separate the inner lumen of the main membrane into a main opening and at least one first sub-opening. The first sub-opening is in sealed connection with the distal end of the branch membrane, and an included angle between a plane defined by the first sub-opening and a plane defined by the main opening is greater than 0°.

The present disclosure further provides a vascular stent, which includes a main body stent, a branch tube stent, and a vascular shunt stent, wherein the vascular shunt stent includes a main body tube and at least one branch tube axially inserted into an inner lumen of the main body tube. The main body tube includes a tubular main membrane, at least one branch tube includes a tubular branch membrane, and the branch membrane is accommodated in an inner lumen of the main membrane. A first sealing film is arranged between a distal end of the main membrane and a distal end of the branch membrane to separate the inner lumen of the main membrane into a main opening and at least one first sub-opening. The first sub-opening is in sealed connection with the distal end of the branch membrane, and an included angle between a plane defined by the first sub-opening and a plane defined by the main opening is greater than 0°; one end of the main body stent is inserted into the main body tube of the vascular shunt stent through the main opening on the first sealing film, and one end of the branch tube stent is inserted into the branch tube through the sub-opening on the first sealing film.

The first sealing film is arranged between the distal end of the main membrane and the distal end of the branch membrane of the vascular shunt stent provided in the present disclosure, to separate the inner lumen of the main membrane into the main opening and the at least one first sub-opening. The plane defined by the first sub-opening intersects with the plane defined by the main opening. The distal end of the branch membrane is in sealed connection with a periphery of the first sub-opening. Since the main opening and the first sub-opening are not on the same plane, that is, orientations of the main opening and the first sub-opening are different, the main body stent and the branch tube stent can be inserted into the main opening and the first sub-opening correspondingly from different directions conveniently, which facilitates the operation and use.

BRIEF DESCRIPTION OF THE DRAWINGS

In order to illustrate the technical solution of embodiments of the present disclosure more clearly, accompanying drawings required in the embodiments are briefly introduced below. Apparently, the accompanying drawings in the following description are some embodiments of the present disclosure. Those ordinarily skilled in the art may obtain other accompanying drawings according to these accompanying drawings without creative efforts.

FIG. 12 is a schematic perspective view showing a structure of a vascular shunt stent according to a fourth embodiment of the present disclosure.

FIG. 13 is a schematic perspective view showing a structure of the vascular shunt stent in FIG. 12, viewed from another aspect.

FIG. 14 is a schematic perspective view showing a structure of one of the leakage preventing members in FIG. 12.

FIG. 27 is a schematic perspective view showing a structure of one of the branch tubes in FIG. 26.

FIG. 28 is a schematic perspective view showing a structure of a wave-shaped support member in FIG. 27.

FIG. 29 is a schematic perspective view showing a structure of a vascular shunt stent according to a sixteenth embodiment of the present disclosure.

DESCRIPTION OF THE EMBODIMENTS

The technical solution in embodiments of the present disclosure will be described clearly and completely concerning the accompanying drawings in the embodiments of the present disclosure. The described embodiments are only a part of the embodiments of the present disclosure, but not all of them. Based on the embodiments of the present disclosure, all other embodiments obtained by those ordinarily skilled in the art without creative labor should fall in the protective scope of the present disclosure.

In addition, the descriptions of the following embodiments refer to accompanying drawings to exemplify specific embodiments that the present disclosure can be implemented with. Directional terms mentioned in the present disclosure, such as "up", "down", "front", "rear", "left", "right", "inside", "outside", "side", etc., only refer to the direction of the accompanying drawings. Therefore, the directional terms are used to explain and understand the present disclosure better and more clearly, not to indicate or imply that the apparatus or element referred to must have a specific orientation or must be constructed and operated in a specific orientation, and therefore cannot be understood as a limitation on the present disclosure.

In the description of the present disclosure, the term "proximal end" in the present disclosure refers to an end near the heart, and the term "distal end" refers to an end away from the heart. The terms "high" and "low" described in the present disclosure are illustrated relative to the main membrane. An end surface exceeding the main membrane is defined as high, and an end surface that does not exceed the main membrane is defined as low. The definitions are only for convenience in expression and cannot be understood as limitations on the present disclosure.

Figure 1:
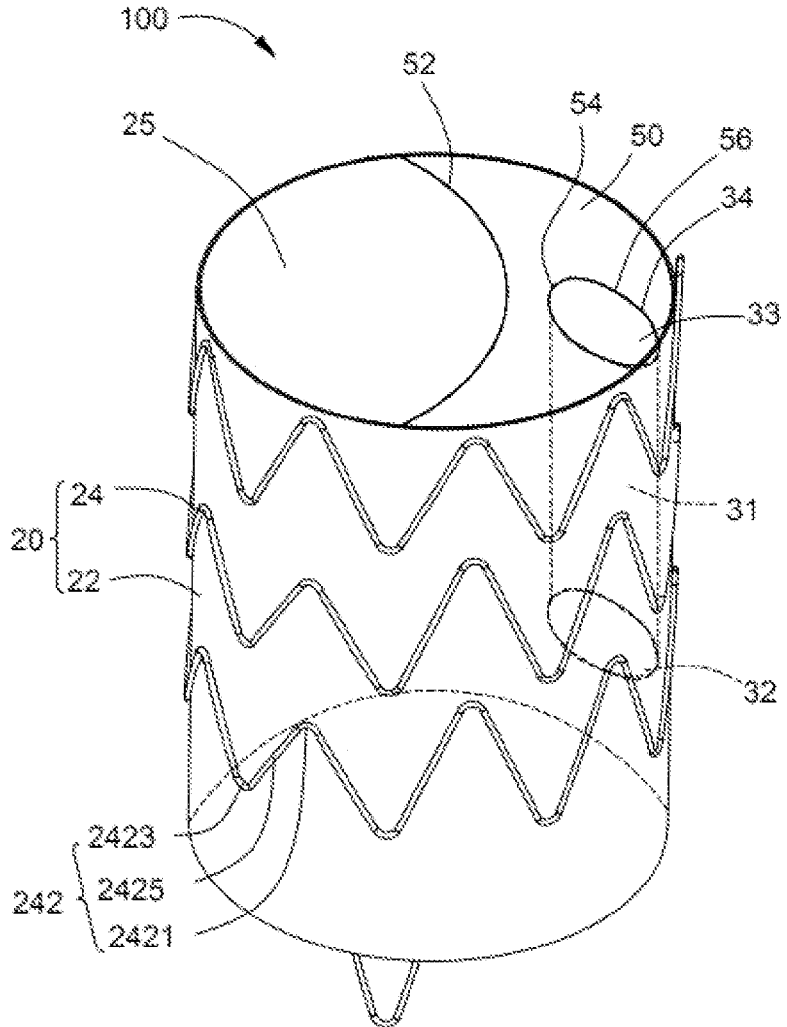
FIG. 1 is a schematic perspective view showing a structure of a vascular shunt stent according to a first embodiment of the present disclosure.
Figure 2:
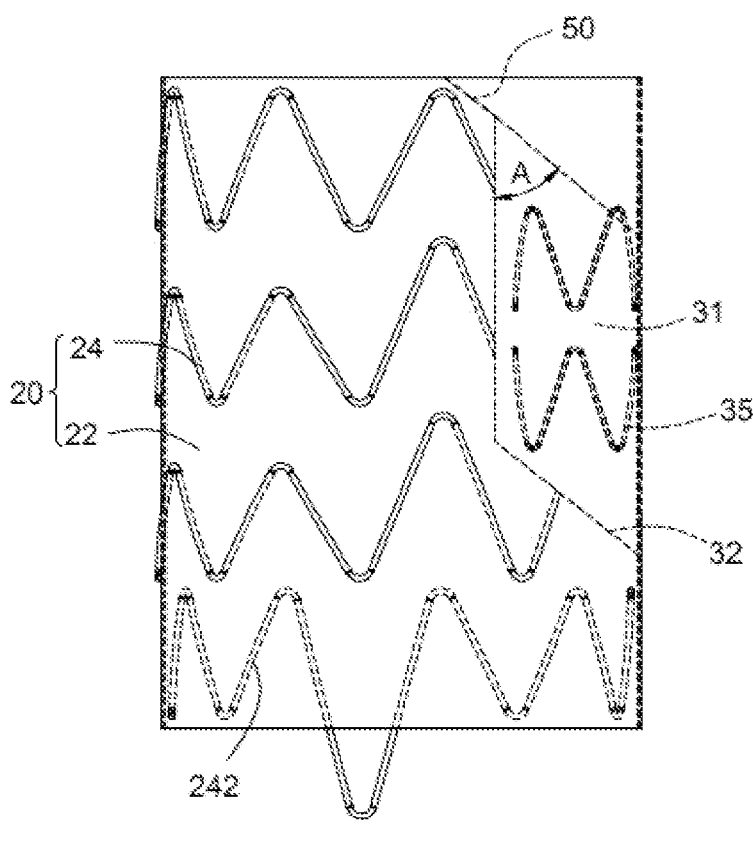
FIG. 2 is a side view of the vascular shunt stent of FIG. 1.
Figure 3:
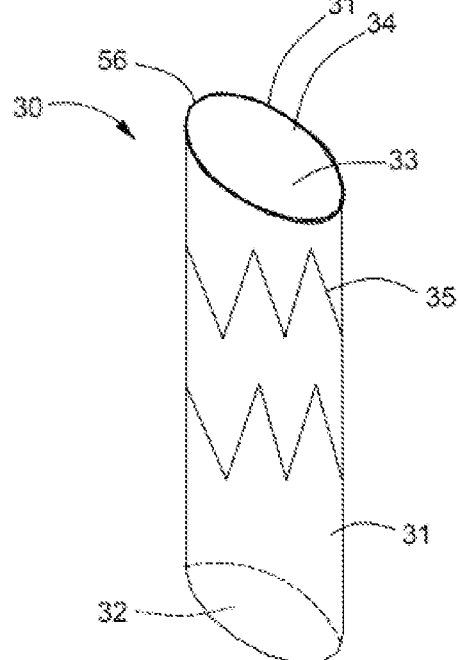
FIG. 3 is a schematic perspective view showing a structure of one of the branch tubes in FIG. 1.

Reference is made to FIG. 1 and FIG. 2, wherein FIG. 1 is a schematic perspective view showing a structure of a vascular shunt stent according to a first embodiment of the present disclosure, FIG. 2 is a side view of the vascular shunt stent in FIG. 1, and FIG. 3 is a schematic perspective view of the structure of one branch tube 30 in FIG. 1. The present disclosure provides a vascular shunt stent 100, which includes a main body tube 20 and at least one branch tube 30 axially inserted into an inner lumen of the main body tube 20. The main body tube 20 includes a tubular main membrane 22. At least one branch tube 30 includes a tubular branch membrane 31. The branch membrane 31 is accommodated in the inner lumen of the main membrane 22. A first sealing film 50 is arranged between a distal end of the main membrane 22 and a distal end of the branch membrane 31 to divide the inner lumen of the main membrane 22 into a main opening 52 and at least one first sub-opening 54. The first sub-opening 54 is in sealed connection with the distal end of the branch membrane 31. An included angle between a plane defined by the first sub-opening 54 and a plane defined by the main opening 52 is greater than 0°, that is, the plane defined by the first sub-opening 54 is not parallel to the plane defined by the main opening 52, i.e., the plane defined by the first sub-opening 54 intersects with the plane defined by the main opening 52. The main opening 52 and the first sub-opening which are not parallel to each other can be more easily distinguished when being not incompletely released in a process of implanting the stent, which is convenient for a surgeon to identify the main opening 52 and the first sub-opening 54.

The first sealing film 50 is arranged between the distal end of the main membrane 22 and the distal end of the branch membrane 22 of the vascular shunt stent 100 in the present disclosure, to divide the inner lumen of the main membrane 22 into the main opening 52 and the at least one first sub-opening 54, the plane defined by the first sub-opening 54 intersects with the plane defined by the main opening 52, and the distal end of the branch membrane 31 is in sealed connection with the periphery of the first sub-opening 54. Since the main opening 52 and the first sub-opening 54 are not coplanar, that is, orientations of the main opening 52 and the first sub-opening 54 are different, the main opening 52 is provided in a plane perpendicular to the axis of the main body tube 20, which brings the convenience for implanting the main body stent and stably fixing the main body stent. The first sub-opening 54 is provided in a plane that is not perpendicular to the axis of the main body tube 20, that is, disposed inclinedly with respect to the main opening 52. The first sub-opening 54 provided inclinedly facilitates the entry of a guide wire and the delivery of a branch stent sheath, thereby bringing more convenience for quickly implanting the branch stent. Further, the main opening 52 and the first sub-opening 54 are arranged on different planes, that is, they have different orientations, which is convenient for inserting the main body stent and the branch tube stent (that is, the branch stent) quickly into the corresponding main opening 52 and the corresponding first sub-opening 54 from different directions, which brings the convenience for operation and use.

In this embodiment, the plane defined by the main opening 52 is perpendicular to the axis of the main body tube 20, and the included angle between the plane defined by the first sub-opening 54 and the axis of the main body tube 20 is less than 90°. Specifically, the first sealing film 50 extends inclinedly from the middle of the main opening 52 towards the proximal end thereof until it is connected to an inner surface of the main body tube 20, such that the included angle between the first sealing film 50 and the axis of the main body tube 20 is less than 90°. Since the first sub-opening 54 is provided in the first sealing film 50, the included angle A between the plane defined by the first sub-opening 54 and the axis of the main body tube 20 is greater than 0° and less than 90°.

Preferably, the included angle A between the plane defined by the first sub-opening 54 and the axis of the main body tube 20 is greater than 5° and less than 80°. More preferably, the included angle A is greater than 30° and less than 60°.

The proximal end of the branch membrane 31 is provided with a second sub-opening 32, and the plane defined by the first sub-opening 54 is parallel to a plane defined by the second sub-opening 32. The branch membrane 31 has a distal sub-opening 34 corresponding to the first sub-opening 54. When the distal end of the branch membrane 31 is connected to the first sealing film 50, a periphery of the distal sub-opening 34 is in sealed connection with a periphery of the first sub-opening 54.

Preferably, the first sub-opening 54 is provided with an annular support member 56 there around and/or the second sub-opening 32 is provided with an annular support member 56 there around, and the annular support members 56 are configured to expand the first sub-opening 54 and the second sub-opening 32, which bring convenience for inserting a branch tube stent. In this embodiment, the annular support member 56 is a supporting ring, which is configured to expand the branch membrane 31 to maintain the branch membrane 31 in a tubular shape. When the first sub-opening 54 is inserted with the branch tube stent, the annular support member 56 at the periphery of the first sub-opening 54 is capable of fixing the branch tube stent within the branch tube 30, that is, the first sealing film 50 can be attached to an outer surface of the branch tube stent in a sealed manner by the supporting ring, to prevent endoleak. In addition, the branch tube 30 may provide an elongated proximal anchoring region for the branch tube stent, which further confines the branch tube stent, and increases the stability of the branch tube stent after being released. The axial length of the branch tube 30 may be less than, greater than, or equal to that of the main body tube 20. In the case that multiple branch tubes 30 are provided in the same vascular shunt stent 100, the first sealing film 50 is provided with a supporting ring at the distal end of each branch tube 30. The lengths of the branch tubes 30 may be the same or different. The included angle between the plane defined by the first sub-opening 54 and the plane defined by the main opening 52 is greater than 0°, that is, the first sub-opening 54 is not perpendicular to the axis of the main body tube 20. When the vascular shunt stent 100 is compressed and crimped in a delivery sheath or not completely released, it will be subjected to a pressure perpendicular to the axis of the main body tube 20, that is, the first sub-opening 54 will be subjected to a pressure perpendicular to the axis of the main body tube 20. When the first sub-opening 54 is arranged perpendicular to the axis of the main body tube 20, the first sub-opening 54 severely deforms when being compressed by the pressure. After the vascular shunt stent 100 is completely released, the first sub-opening 54 cannot be quickly restored completely in shape, such that the branch stent is difficult to implant. When the first sub-opening 54 and the axis of the main body tube 20 are not arranged perpendicularly, the pressure to which the first sub-opening 54 is subjected will not compress the sub-opening 54 perpendicularly, and will not cause the sub-opening 54 and even the annular support member 56 on the sub-opening 54 to severely deform. After the vascular shunt stent 100 is completely released, the first sub-opening 54 and the annular support member 56 on the first sub-opening 54 can be easily restored completely, which brings the convenience for quickly implanting the branch stent.

In other embodiments, the distal sub-opening 34 and the second sub-opening 32 of the branch membrane 31 are both provided with annular support members 56 at the peripheries thereof.

As shown in FIG. 1, the main body tube 20 further includes a supporting frame 24 fixed on the wall surface of the main membrane 22. The branch tube 30 is enclosed by the tubular branch membrane 31, such that the inner lumen of the main body tube 20 is separated into the main body tube inner lumen 25, and a branch tube inner lumen 33. The second sub-opening 32 is positioned at the proximal end of the branch tube inner lumen 33, and the distal sub-opening 34 is positioned at the distal end of the branch tube inner lumen 33. The distal end of the main body tube inner lumen 25 is communicated with the main opening 52. The distal end of the branch tube inner lumen 33 is communicated with the first sub-opening 54. The main body tube 20 is the main structure of the vascular shunt stent 100, and the transverse end surface of the main body tube 20 is circular or elliptical and adapted to a blood vessel. The supporting frame 24 is stitched on the main membrane 22, and the supporting frame 24 is formed by arranging a plurality of annular wave-shaped support rods 242 along the axial direction of the main membrane 22. Each annular wave-shaped support rod 242 may be an equal-height-wave support rod or a high-low-wave support rod, and the equal-height-wave support rod means that peaks on the annular wave-shaped support rod are at the same height and valleys thereof are at the same height as well, that is, the peaks are located at the same level and the valleys are located at the same level. The high-low-wave support rod means that peaks on the annular wave-shaped support rod 242 are at different heights and valleys may be at different heights as well.

The supporting frame 24 includes a plurality of annular sinusoidal wave-shaped support rods 242, and these annular wave-shaped support rods 242 are arranged at intervals along the axial direction of the main membrane 22. Each sinusoidal waveform of each of the annular wave-shaped support rods 242 includes a peak 2421, a valley 2423, and a connecting rod 2425 connected between the peak 2421 and the valley 2423. Each annular wave-shaped support rod 242 is woven from a super-elastic nickel-titanium wire, which has a wire diameter (i.e., diameter) selectively ranging from 0.1 mm to 0.6 mm. A connecting sleeve is provided for each of the annular wave-shaped support rods 242, and the connecting sleeve connects two opposite ends of the annular wave-shaped support rod 242, that is, two opposite ends of the annular wave-shaped support rod 242 are both received within the connecting sleeve, and then two ends of the nickel-titanium wire are fixed inside the connecting sleeve by mechanical pressing or welding.

In this embodiment, the annular wave-shaped support rod 242 is woven from a nickel-titanium wire with a diameter of 0.5 mm, the number of the sinusoidal waves is nine, and the axial length of the annular wave-shaped support rod 242 is ranged from 6 mm to 15 mm.

In other embodiments, the number of the sinusoidal waves may be other numbers, and the axial length of the annular wave-shaped support rod 242 may be any value.

In other embodiments, the supporting frame 24 may be of a woven mesh structure or a mesh structure formed by cutting.

The main membrane 22 and the branch membrane 31 are both made of polyester cloth, PTFE, PET, or other polymer materials, and the supporting frame 24 is stitched on the main membrane 22 by a suture. The suture can follow the wave course of each of the annular wave-shaped support rods 242 and accompany the entire supporting frame 24. The suture can stitch each of the annular wave-shaped support rods 242 on the main membrane 22 by several suture knots which are arranged non-equidistantly.

The branch tube inner lumen 33 is defined by the branch membrane 31 independently, and a space between the branch membrane 31 and the main membrane 22 is the main body tube inner lumen 25. With this design, when the vascular shunt stent 100 is compressed and crimped, the overall diameter of the vascular shunt stent 100 can be reduced, such that the diameter of a delivery system for assembling the sheath can be reduced and the delivery of the vascular shunt stent 100 is facilitated. The diameter of the main body tube inner lumen 25 is larger than that of the branch tube inner lumen 33, and the number of the branch tube 30 can be set according to actual requirements, generally one to four, preferably one to three. The first sealing film 50 is provided with one to four first sub-openings 54, preferably two to four first sub-openings 54 corresponding to the branch tubes 30. Transverse end surfaces of the main body tube inner lumen 25 and the branch tube inner lumen 33 are circular, elliptical, fusiform, or irregularly curved.

In this embodiment, the number of the branch tubes 30 is one. The branch tube 30 contacts the inner surface of the main body tube 20, and the distal end of the branch tube 30 is communicated with the first sub-opening 54.

The main opening 52 and the first sub-opening 54 are both provided in the first sealing film 50, and the distal end of the branch membrane 31 is connected to the first sealing film 50 corresponding to the first sub-opening 54 in a sealed manner. That is, the first sealing film 50 connects the main membrane 22 with the branch membrane 31 together, and closes the gap between the inner wall of the main body tube 20 and the outer wall of the branch tube 30. The opening area of the main opening 52 is smaller than the radial cross-sectional area of the main membrane 22, the opening area of the first sub-opening 54 is smaller than that of the main opening 52, and the opening area of the main opening 52 is larger than that of a single sub-opening 54. Preferably, the ratio of the opening area of the main opening 52 to the opening area of the single sub-opening 54 is ranged from 3:1 to 6:1. Further, the opening area of the main opening 52 is greater than the sum of the opening areas of all the sub-openings 54, such that more sufficient space is provided for a main blood flow opening.

In other embodiments, the opening area of the main opening 52 may be the same as that of the first sub-opening 54.

As shown in FIG. 3, a wave-shaped support member 35 is fixed on the branch membrane 31 of each branch tube 30. The wave-shaped support member 35 can increase the supporting strength of the branch tube 30 and avoid poor blood flow or even blood flow blocking caused by the condition that the connected branch tube stent is pressed by the main body stent. The wave-shaped support member 35 can be set depending on the shape of the branch membrane 31. That is, one wave-shaped support member 35 may be fixed on the branch membrane 31, or a plurality of wave-shaped support members 35 may be arranged on the branch membrane 31 at several intervals along the axial direction thereof, and these wave-shaped support members 35 collectively form a branch tube supporting frame of the branch membrane 31. In this embodiment, the distal end of at least one wave-shaped support member 35 is adjacent to the annular support member 56. Preferably, the distal end of at least one wave-shaped support member 35 is connected to the annular support member 56.

The wave-shaped support member 35 may be annular or open-loop, and the structure, shape, and material of the wave-shaped support member 35 are similar to those of the annular wave-shaped support rod 242 on the main body tube 20, which will not be repeated here.

In other embodiments, a woven mesh branch tube supporting frame may be fixed on the branch membrane 31 as well.

In other embodiments, the branch membrane 31 may be of a semi-tubular structure, and the branch membrane 31 with the semi-tubular structure is stitched on the inner surface of the main membrane 22, to form a semicircular branch tube together with the main membrane 22.

Figure 4:
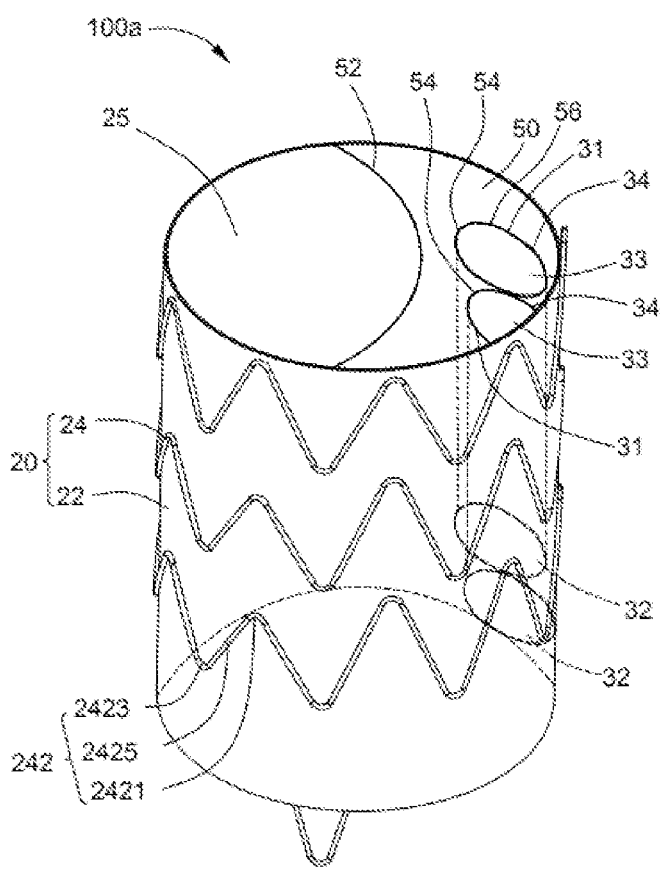
FIG. 4 is a schematic perspective view showing a structure of a vascular shunt stent according to a second embodiment of the present disclosure.
Figure 5:
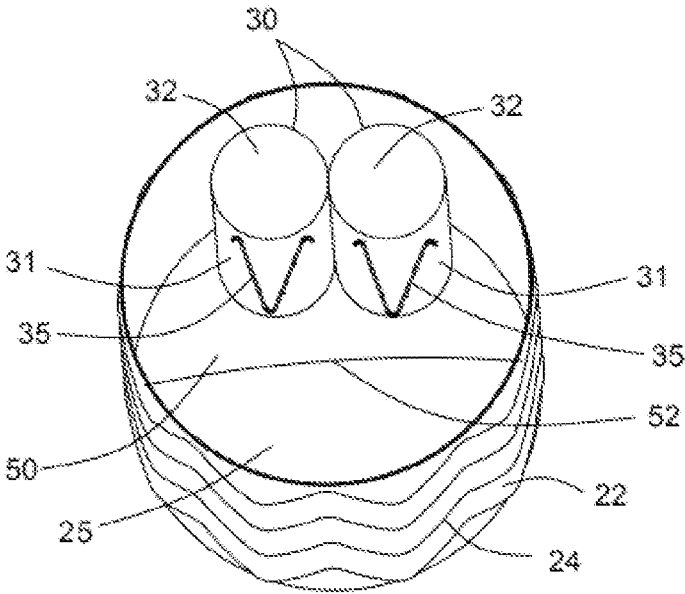
FIG. 5 is a schematic perspective view showing a structure of the vascular shunt stent in FIG. 4, viewed from another aspect.

Referring to FIG. 4 and FIG. 5, wherein FIG. 4 is a schematic perspective view showing a structure of a vascular shunt stent 100 according to a second embodiment of the present disclosure, and FIG. 5 is a schematic perspective view of a structure of the vascular shunt stent 100 in FIG. 4 viewed from another aspect. The vascular shunt stent 100a provided in the second embodiment of the present disclosure has a structure similar to that of the first embodiment, with differences in that in the second embodiment, two branch tubes 30 are axially inserted into a main body tube 20, each of branch tubes 30 includes a tubular branch membrane 31, outer peripheral surfaces of the two branch membranes 31 are adjacent; the two branch membranes 31 are accommodated in an inner lumen of the main membrane 22, a first sealing film 50 is arranged at a distal end of the main membrane 22 and distal ends of the two branch membranes 22, the first sealing film 50 is provided with two first sub-openings 54, distal sub-openings 34 of the two branch membranes 31 are respectively connected to the two first sub-openings 54 of the first sealing film 50 in a sealed manner, and proximal ends of the two branch membranes 31 are respectively provided with second sub-openings 32. An included angle between a plane defined by each of the first sub-openings 54 and an axis of the main body tube 20 is less than 90°. The planes defined by the two first sub-opening 54 may be or may not be parallel. In this embodiment, the planes defined by the two first sub-openings 54 are parallel to the planes defined by the two second sub-openings 32.

In other embodiments, axial lengths of the two branch membranes 31 may be the same or different, and the planes defined by the second sub-openings 32 of the two branch membranes 31 may be or may not be coplanar.

Figures 6, 7:
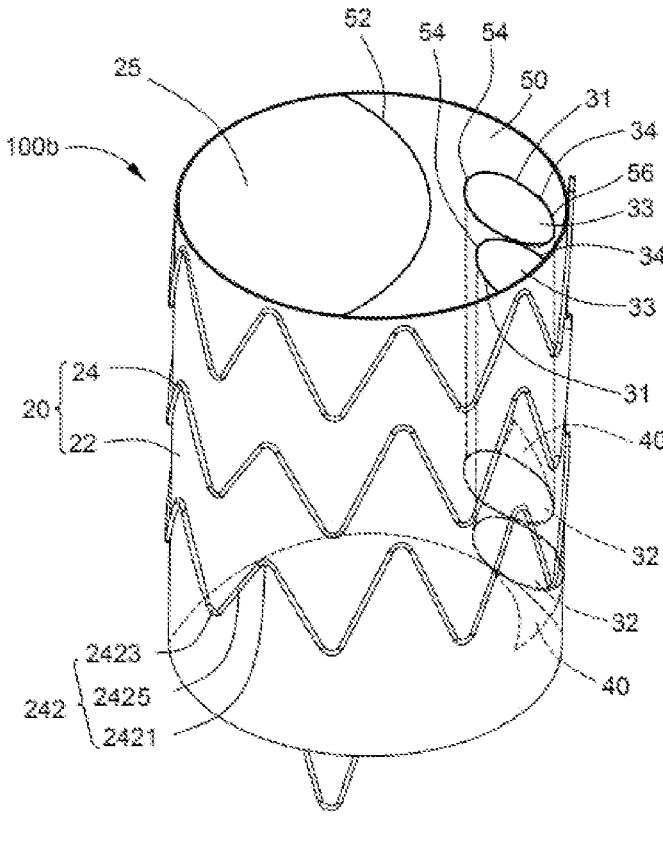
FIG. 6 is a schematic perspective view showing a structure of a vascular shunt stent according to a third embodiment of the present disclosure.
FIG. 7 is a schematic perspective view showing a structure of the vascular shunt stent in FIG. 6, viewed from another aspect.
Figure 8:
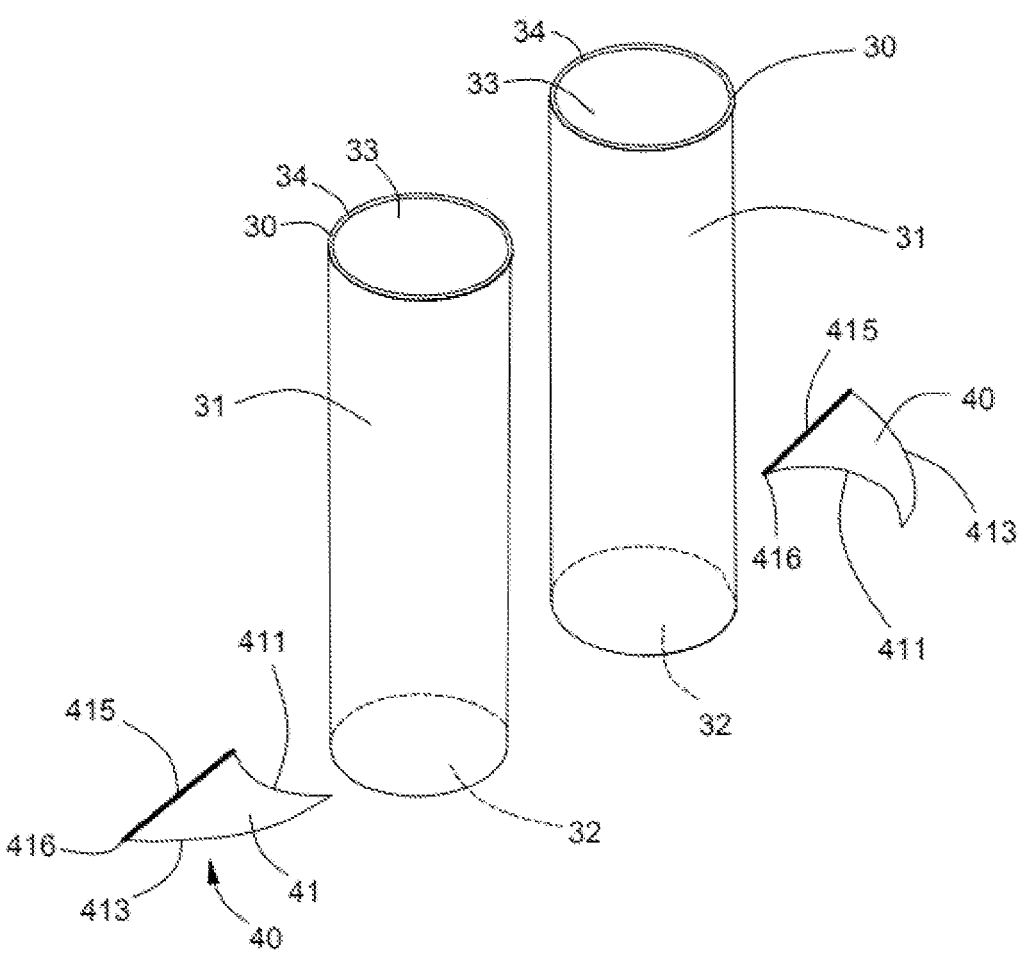
FIG. 8 is a schematic exploded perspective view showing structures of leakage preventing members and branch tubes of the vascular shunt stent according to the third embodiment of the present disclosure.

Referring to FIG. 6 to FIG. 8, wherein FIG. 6 is a schematic perspective view showing a structure of a vascular shunt stent 100b according to a third embodiment of the present disclosure, FIG. 7 is a schematic perspective view of a structure of the vascular shunt stent 100b in FIG. 6 viewed from another aspect, and FIG. 8 is a schematic exploded perspective view of a leakage preventing member 40 and a branch tube 30 of the vascular shunt stent 100b according to the third embodiment of the present disclosure. The structure of the vascular shunt stent 100b provided by the third embodiment of the present disclosure is similar to that of the second embodiment, with a difference in that: the branch membrane 31 is provided with a leakage preventing member 40 between the periphery of the second sub-opening 32 and the main membrane 22.

The vascular shunt stent 100b provided in this embodiment is provided with the leakage preventing member 40 between the periphery of the second sub-opening 32 of the branch membrane 31 and the inner surface of the main membrane 22, and the first sealing film 50 is arranged between the distal end of the main membrane and the distal end of the branch membrane 22. Therefore, when the main body stent is inserted into the main opening 52 of the main body tube 20, the edge of the first sealing film 50 can be tightly attached to the outer surface of the main body stent 800, and the edge of the leakage preventing member 40 can be tightly attached to the outer surface of the main body stent 800, such that the distal end and the proximal end of the vascular shunt stent 100b are tightly attached to the outer surface of the main body stent inserted into the main opening 52, and thus the endoleak can be effectively prevented.

The leakage preventing member 40 is a leakage preventing sheet connected to the periphery of the second sub-opening 32, and the leakage preventing sheet is configured to seal the gap between the main membrane 22 and the branch membrane 31. Specifically, the leakage preventing member 40 may be formed by a plurality of leakage preventing sheets splicing together, and these leakage preventing sheets are respectively connected between the inner surface of the main membrane 22 and the outer surface of the branch membrane 31 in a sealed manner and cooperatively enclose a through hole. A periphery of the through hole of the leakage preventing member 40 is attached to the outer surface of the branch membrane 31 in a sealed manner. Preferably, the periphery of the through hole of the leakage preventing member 40 is connected to the edge of the second sub-opening 32 in a sealed manner, and an outer periphery of one side of the leakage preventing member 40 away from the main opening 52 is connected to the inner surface of the main membrane 22 in a sealed manner.

In other embodiments, the through hole defined by the leakage preventing sheets is not a complete through hole, which may be only connected to the left side and the right side of the branch membrane 31 in a sealed manner. The rear side of the branch membrane 31 is in sealed connection to the main membrane 22. The front side of the branch membrane 31 can be snapped with the main body stent in a sealed manner after the main body stent being implanted therein.

In this embodiment, the leakage preventing member 40 includes two leakage preventing sheets, each of the leakage preventing sheets is a leakage preventing membrane 41, and the two leakage preventing membranes 41 are respectively in sealed connection between the edge of the second sub-opening 32 of the branch membrane 31 and the inner surface of the main membrane 22. That is, two opposite sides of the proximal end of the branch membrane 31 are respectively provided with a leakage preventing membrane 41, and each of the leakage preventing membranes 41 is connected between the branch membrane 31 and the main membrane 22. Through the design of the laminar leakage preventing sheet, the position of the leakage preventing member can be set more flexibly, and the usage of the membranes of the vascular shunt stent can be reduced in general, such that the diameter of the delivery sheath is reduced. Meanwhile, the structure of the leakage preventing member 40 is relatively small, and the smoothness of blood flow will not be affected in the release process.

As shown in FIG. 8, each of the leakage preventing membranes 41 is a leakage preventing membrane sheet having a three-side shape, and each of the leakage preventing membranes 41 includes a first edge 411, a second edge 413, and a third edge 415 connected end to end in sequence. The first edge 411 of the leakage preventing membrane sheet 41 is in sealed connection with the branch membrane 31, the second edge 413 of the leakage preventing membrane 41 is in sealed connection with the main membrane 22, and the third edge 415 of the leakage preventing membrane 41 is in sealed connection between the branch membrane 31 and the main membrane 22. Preferably, the first edge 411 of each of the leakage preventing membranes 41 is a curved edge corresponding to the outer surface of the branch membrane 31, that is, the center of the first edge 411 is positioned on the axis of the branch membrane 31. The second edge 413 is a curved edge corresponding to the inner surface of the main membrane 22, that is, the center of the second edge 413 is positioned on the axis of the main membrane 22. The third edge 415 can be a straight edge or a curved edge.

Preferably, the third edge 415 of each of the leakage preventing membranes 41 is provided with an elastic first support member 416, the first support member 416 extends along the third edge 415, and two opposite ends of the first support member 416 are respectively connected to the branch membrane 31 and the main membrane 22. When the vascular shunt stent 100 is unfolded, the first support member 416 is configured to support the leakage preventing membrane 41 to retain an unfolded state, preventing collapse of the membrane 41 which may cause interference with the implantation of the main body stent. When the main body stent is inserted into the main opening 52, the first support member 416 can be tightly attached to the outer surface of the main body stent 800, such that the third edge 415 of each of the leakage preventing membranes 41 is tightly attached to the outer surface of the main body stent 800 to prevent endoleak. Specifically, the first support member 416 is an elastic support rod, and the elastic support rod is disposed on the third edge 415 and extends along the length direction of the third edge 415.

In other embodiments, one of the first edge 411 and the second edge 413 of each of the leakage preventing membranes 41 is provided with an elastic second support member, and the second support member is connected to the branch membrane 31 or the main membrane 22. The third edge 415 is also provided with an elastic first support member 416. The second support member is connected with one end of the first support member 416, such that the leakage preventing membrane 41 is supported to be in an unfolded state when the vascular shunt stent 100 is unfolded. Preferably, the second support member is an elastic support rod.

In other embodiments, the first edge 411, the second edge 413 and the third edge 415 of each of the leakage preventing membranes 41 are each provided with an elastic support member, that is, three support members extend along respective length directions of the first edge 411, the second edge 413 and the third edge 415. The three support members are connected end to end. The support member on the first edge 411 is connected to the branch membrane 31, the support member on the second edge 413 is connected to the main membrane 22, and the support member on the third edge 415 is connected between the branch membrane 31 and the main membrane 22, such that the leakage preventing cover 41 is supported to be in an unfolded state when the vascular shunt stent 100 is unfolded. Preferably, each of the support members is an elastic support rod.

In other embodiments, the leakage preventing membrane 41 can be connected to the left side and the right side of the branch membrane 31 by stitching or other flexibly securing, for example, by fixedly connecting, with the rear side of the branch membrane 31 being connected to the main membrane 22. A preferred fixed connection manner is stitching connection. By stitching the two edges, the shape of the third edge can be stabilized to a certain extent. Alternatively, a loop of thread can be stitched on the third edge to reinforce the supporting performance. Such a method can reduce the diameter of the sheath. Moreover, the overall flexibility of the shunt stent will be better.

Figure 9:
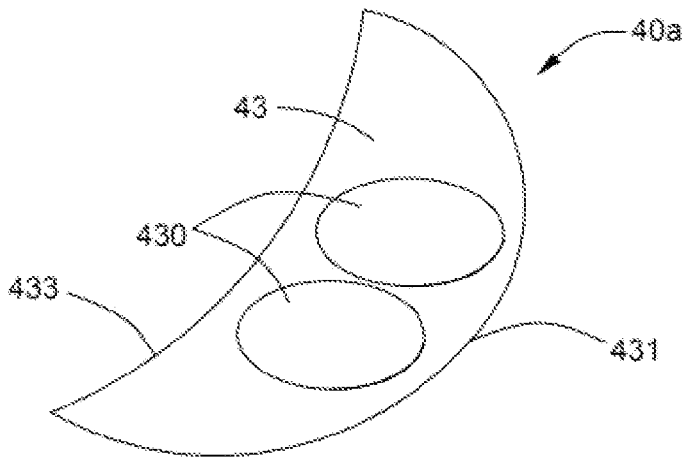
FIG. 9 is a schematic view showing a structure of another embodiment of the leakage preventing member of the vascular shunt stent according to the third embodiment of the present disclosure.

As shown in FIG. 9, FIG. 9 is another embodiment of a leakage preventing member 40a of the vascular shunt stent 100b according to the third embodiment of the present disclosure. The leakage preventing member 40a is a single-piece leakage preventing sheet, and the leakage preventing sheet is a leakage preventing membrane 43. The central portion of the leakage preventing membrane 43 is provided with two through holes 430 adjacent to each other. Edges of the through holes 430 of the leakage preventing membrane 43 are attached to the outer surface of the corresponding branch membrane 31 in a sealed manner, and an outer peripheral edge of the leakage preventing membrane 43 facing away from the main opening 52 is in sealed connection with the inner surface of the main membrane 22. Preferably, the leakage preventing membrane 43 is crescent, which includes a first curved edge 431 facing the inner surface of the main membrane 22 and a second curved edge 433 facing away from the first curved edge 431. The first curved edge 431 of the leakage preventing membrane 43 is in sealed connection with the main membrane 22, and the second curved edge 433 is in sealed connection with the outer surface of the main body stent inserted in the main opening 52 of the main body tube 20.

Preferably, the first curved edge 431 and/or the second curved edge 433 of the leakage preventing member 40a are/is provided with an elastic support member. The support member on the first curved edge 431 is connected to the inner surface of the main membrane 22. The support member on the second curved edge 433 is tightly attached to the outer surface of the main body stent inserted in the main opening 52 of the main body tube 20. Further, the support member is an elastic support rod, and the support rod extends along the first curved edge 431 and/or the second curved edge 433.

In other embodiments, the central portion of the leakage preventing membrane 43 is provided with three or more through holes. Three or more branch tubes 30 are accommodated in the inner lumen of the main membrane 22. Three or more first sub-openings 54 are provided in the first sealing film 50. The distal sub-opening 34 of each of the branch tubes 30 is in sealed connection with the corresponding first sub-opening 54 of the first sealing film 50. The second sub-opening 32 of each of the branch tubes is in sealed connection in the corresponding through hole 430 of the leakage preventing membrane 43.

Figure 10:
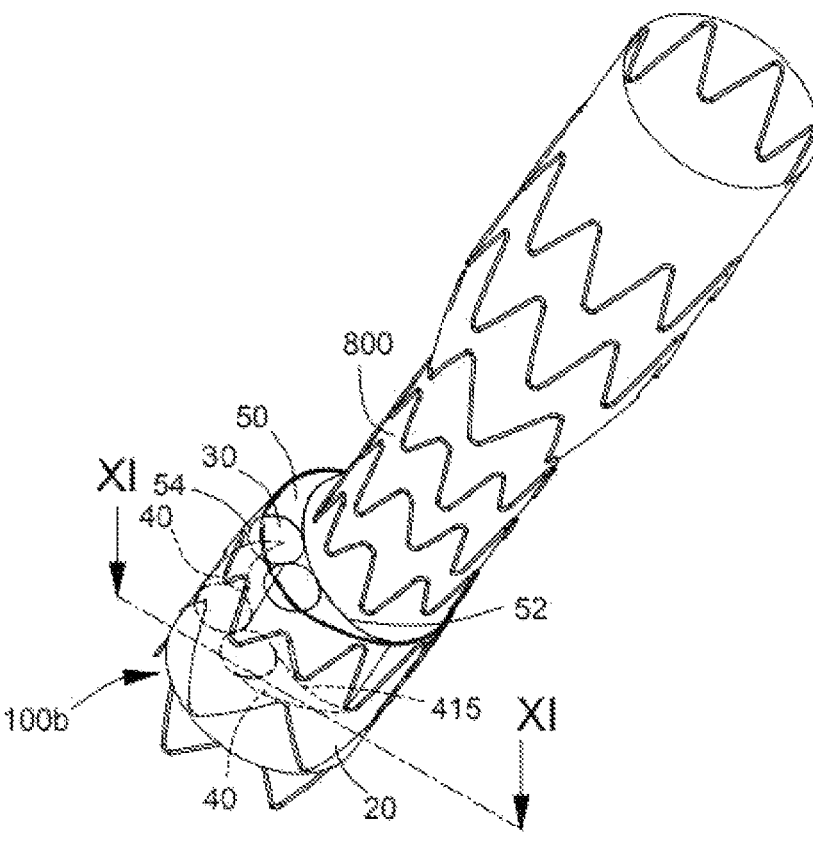
FIG. 10 is a schematic perspective view showing a structure of the vascular shunt stent in one of operating states according to the third embodiment of the present disclosure.
Figure 11:
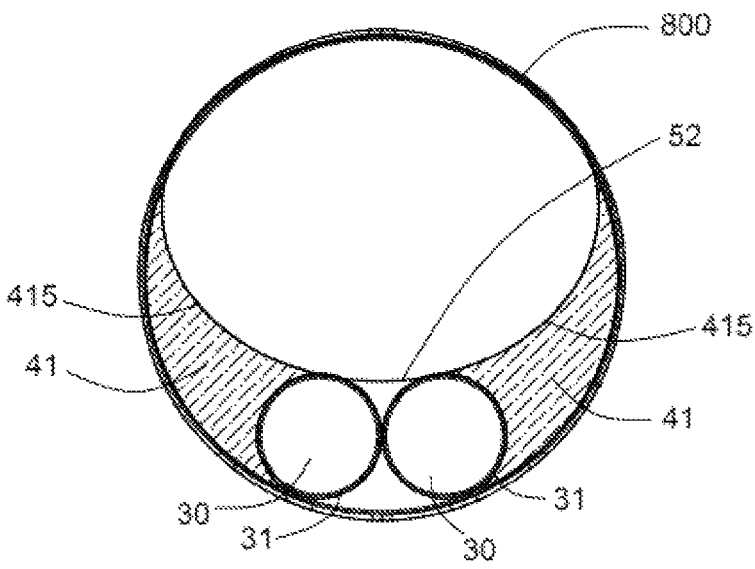
FIG. 11 is a cross-sectional view taken along a line XI-XI in FIG. 10.

Reference is made to FIG. 10 and FIG. 11, wherein FIG. 10 is a schematic perspective view of a structure of the vascular shunt stent 100b in one of the operating states according to the third embodiment of the present disclosure, and FIG. 11 is a cross-sectional view taken along a line XI-XI in FIG. 10. When the vascular shunt stent 100b is used, one end of the main body stent 800 is inserted into the main opening 52 of the main body tube 20 from a distal end thereof, the main body stent 800 expands the inner diameter of the main opening 52 of the first sealing film 50, and the first sealing film 50 deforms to enable an edge of the main opening 52 to be tightly attached to an outer surface of the main body stent 800. Meanwhile, the main body stent 800 further expands third edges 415 of two leakage preventing members 40, and each of the leakage preventing members 40 deforms such that the third edge 415 is tightly attached to an outer surface of the main body stent 800. At this time, a distal end and a proximal end of each of the branch tubes 30 are sealed by the first sealing film 50 and the leakage preventing members 40 respectively, which can effectively prevent endoleak. At this time, the plane defined by a first sub-opening 54 is inclined to an axis of the main body tube 20, and then a branch tube stent is inserted into a branch tube inner lumen 33 of each of the branch tubes 30 of the vascular shunt stent 100b to form the vascular stent, that is, the vascular stent further includes a vascular shunt stent, the main body stent 800 and the branch tube stent. One end of the main body stent 800 is inserted into the main body tube 20 of the vascular shunt stent through the main opening 52 on the first sealing film 50, the leakage preventing member 40 and the first sealing film 50 are tightly attached to the outer surface of the main body stent 800, and one end of the branch tube stent is inserted into the branch tube 30 of the vascular shunt stent through the first sub-opening 54 on the first sealing film 50. By providing the leakage preventing member 40 between the periphery of the sub-opening of the branch membrane 31 and the inner surface of the main membrane 22, a sealing structure is formed at the proximal end of the vascular stent by the leakage preventing member 40, the main body stent 800 and the branch membrane 31. On the one hand, although the first sealing film 50 can achieve a certain sealing effect to prevent tendoleak of the vascular stent, blood at the proximal end continuously flows towards the first sealing film 50 which may cause the first sealing film 50 to exceed its load limit, which may result in endoleak. By providing the leakage preventing member 40, blood is blocked from the proximal end into which the blood flows, and a dual-sealing effect is achieved together with the first sealing film 50 at the distal end, which can further reduce endoleak. On the other hand, blood is prevented from entering the gap between the branch membrane 31 and the main body stent 800, the distal end of which is provided with the first sealing film 50 where the blood cannot flow and may readily cause thrombus.

Reference is made to FIG. 12 and FIG. 13, wherein FIG. 12 is a schematic perspective view showing a structure of a vascular shunt stent 100c according to a fourth embodiment of the present disclosure, and FIG. 13 is a schematic perspective view of a structure of the vascular shunt stent 100c in FIG. 12 viewed from another aspect. The structure of the vascular shunt stent 100c provided in the fourth embodiment of the present disclosure is similar to that of the third embodiment, with differences in that in the fourth embodiment, leakage preventing members 40c are leakage preventing frames 45 disposed on two opposite sides of the branch membrane 31, the two leakage preventing frames 45 are configured to seal gaps between proximal ends of the branch membrane 31 and the main membrane 22. Specifically, one leakage preventing frame 45 is disposed between one side of one branch membrane 31 away from another branch membrane 31 and an inner surface of the main membrane 22, a distal end surface of the leakage preventing frame 45 is connected to the first sealing film 50, and a proximal end surface of the leakage preventing frame 45 is adjacent to a proximal end surface of the branch membrane 31. Preferably, edges of proximal end surfaces of the leakage preventing frames 45 are in sealed connection with a periphery of a corresponding second sub-opening 32 of the branch membrane 31.

Reference is made to FIG. 14, wherein FIG. 14 is a schematic perspective view of a structure of one of the leakage preventing members 40c in FIG. 12. Each of leakage preventing frames 45 includes a distal end surface 451 attached to the first sealing film 50, a proximal end surface 452 facing away from the distal end surface 451, a first attaching surface 454 attached to the branch membrane 31, a second attaching surface 455 attached to the main membrane 22, and a sealing surface 456 connected among the distal end surface 451, the proximal end surface 452, the first attaching surface 454 and the second attaching surface 455. At least the proximal end surface 452 is provided with a second sealing film 457 and the sealing surface 456 is provided with a third sealing film 458. By providing the third sealing film 458 on the sealing surface 456, the sealing effect of the vascular shunt stent and the main body stent can be further improved, a risk of endoleak due to unsatisfied sealing after the main body stent and the vascular shunt stent are released is prevented. Meanwhile, the leakage preventing frames 45 are designed as a whole, and thus have a stable structure.

When each of the leakage preventing frames 45 is connected between the corresponding branch membrane 31 and the main membrane 22. The second sealing film 457 on a proximal end surface 452 is in sealed connection with the branch membrane 31, the main membrane 22, and the proximal end of the third sealing film 458 of the sealing surface 456. A distal end of the third sealing film 458 on the sealing surface 456 is in sealed connection with the first sealing film 50, and two opposite sides of the third sealing film 458 are in sealed connection with the branch membrane 31 and the main membrane 22. In this case, the distal end surface 451 and the first sealing film 50 share the same membrane, the first attaching surface 454 and the branch membrane 31 share the same membrane, and the second attaching surface 455 and the main membrane 22 share the same membrane. By sharing the membrane at connected surfaces in the vascular shunt stent, the overall membrane of the vascular shunt stent used can be reduced, and thus the diameter of the deliverer sheath is reduced. The second sealing film 457, the third sealing film 458, the branch membrane 31, and the main membrane 22 enclose a sealed frame body, such that the branch membranes 31 and the main membrane 22 are sealed by the leakage preventing frames 45, and thus endoleak is prevented.

In other embodiments, the second sealing film 457 on the proximal end surface 452 and the third sealing film 458 on the sealing surface 456 are formed as a single piece. The design of a single piece makes the whole structure of the leakage preventing frames 45 more stable and the supporting performance better, and the overall shape can be stably maintained even in the absence of a support member. Moreover, no additional connection structure exists between the second sealing film 457 and the third sealing film 458, such that the risk of endoleak is avoided.

In other embodiments, the edges of the third sealing film 458 on the sealing surface 456 are provided with an elastic supporting ring for expanding the leakage preventing frames 45. A periphery of the supporting ring is respectively connected to the first sealing film 50, the branch membrane 31, the main membrane 22, and the second sealing film 457 on the proximal end surface 452.

In other embodiments, the distal end surface 451, the proximal end surface 452, the first attaching surface 454, the second attaching surface 455, and the sealing surface 456 of each of the leakage preventing frame 45 each may be provided with a sealing film. Further, these sealing films may be of an integrated structure.

Figure 15:
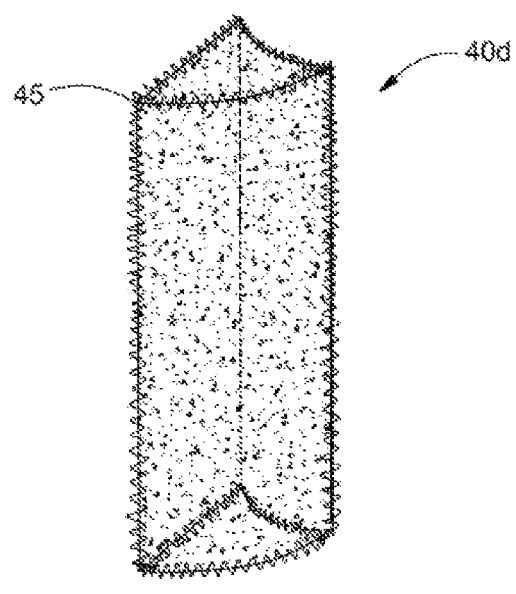
FIG. 15 is a schematic view showing a structure of another embodiment of one of the leakage preventing members of the vascular shunt stent according to the fourth embodiment of the present disclosure.

Reference is made to FIG. 15, wherein FIG. 15 is a schematic view of the structure of another embodiment of one of the leakage preventing members of the vascular shunt stent 100c according to the fourth embodiment of the present disclosure. The structure of the leakage preventing frame 40d in this embodiment is similar to that of the fourth embodiment, with a difference in that the inner lumen of each of leakage preventing frames 40d is filled with an expandable material, or the inner lumen of each of the leakage preventing frames 40d is provided with a villi structure, which can accelerate the formation of thrombus and improve the sealing effect.

Figure 16:
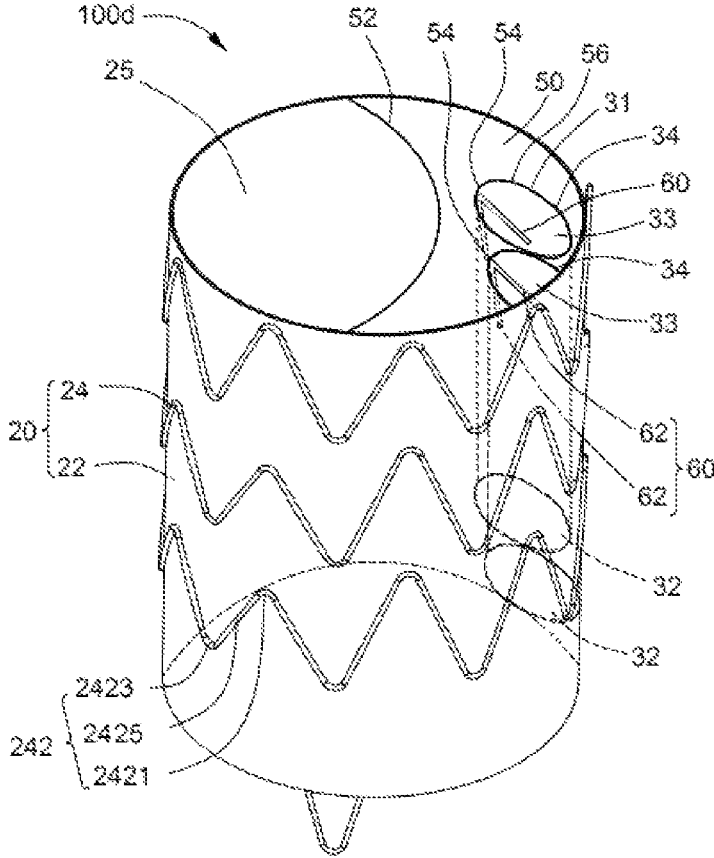
FIG. 16 is a schematic perspective view showing a structure of a vascular shunt stent according to a fifth embodiment of the present disclosure.

Reference is made to FIG. 16, wherein FIG. 16 is a schematic perspective view showing a structure of a vascular shunt stent 100d according to a fifth embodiment of the present disclosure. The structure of the vascular shunt stent 100d provided in the fifth embodiment of the present disclosure is similar to that of the second embodiment, with differences in that a proximal end of an annular support member 56 is arranged adjacent to an edge of one side of the first sealing film 50 away from the main opening 52, at least one support member 60 is provided on a branch membrane 31 of each of branch tubes 30. The support member 60 is located a side of the branch membrane 31 adjacent to the main opening 52, at the distal end of the branch membrane 31. When the vascular shunt stent 100d is in a natural unfolded state, the support member 60 is configured to support the annular support member 56, to maintain the corresponding distal sub-opening 34 in an unfolded state, such that a branch tube stent can be conveniently inserted into the branch tube inner lumen 33 through the distal sub-opening 34.

Specifically, the support member 60 has an inverted V shape, which includes two support rods 62 each having a first end, and the first ends of the two support rods 62 intersect, an intersection of the two support rods 62 is connected to the corresponding annular support member 56, and the two support rods 62 are respectively connected to the branch membrane 31. Each of the support rods 62 is made of a nickel-titanium wire with a wire diameter ranging from 0.10 mm to 0.40 mm, preferably, ranged from 0.20 mm to 0.30 mm. The support rods 62 can be fixed on the branch membrane 31 by stitching or thermal pressing. In this embodiment, the support rod 62 is fixed on the edge of branch membrane 31 by stitching.

Figure 17:
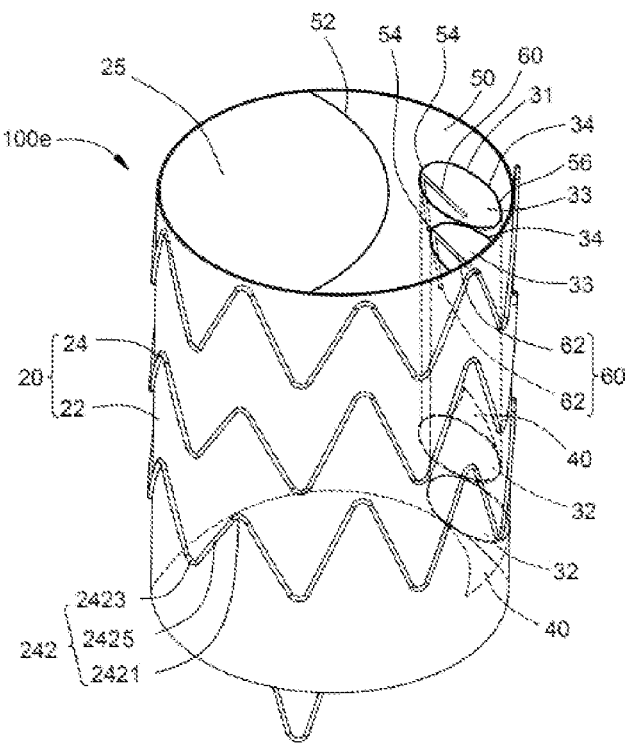
FIG. 17 is a schematic perspective view showing a structure of a vascular shunt stent according to a sixth embodiment of the present disclosure.

Reference is made to FIG. 17, wherein FIG. 17 is a schematic perspective view showing a structure of a vascular shunt stent 100e according to a sixth embodiment of the present disclosure. The structure of the vascular shunt stent 100e provided by the sixth embodiment of the present disclosure is similar to that of the third embodiment, with differences in that a proximal end of an annular support member 56 is arranged adjacent to an edge of one side of the first sealing film 50 away from a main membrane 22, at least one support member 60 is provided on the branch membrane 31 of each of branch tubes 30. When the vascular shunt stent 100e is in a natural unfolded state, the support member 60 is configured to support the annular support member 56, to maintain a corresponding distal sub-opening 34 in an unfolded state, such that a branch tube stent can be conveniently inserted into the branch tube inner lumen 33 through the distal sub-opening 34 easily.

Specifically, the support member 60 has an inverted V shape, which includes two support rods 62 each having a first end, and the first ends of the two support rods 62 intersect, an intersection of the two support rods 62 is connected to the corresponding annular support member 56, and the two support rods 62 are respectively connected to the branch membrane 31. The support rods 62 can be fixed on the branch membrane 31 by stitching or thermal pressing. In this embodiment, the support rods 62 are fixed on an edge of the branch membrane 31 by stitching.

Figure 18:
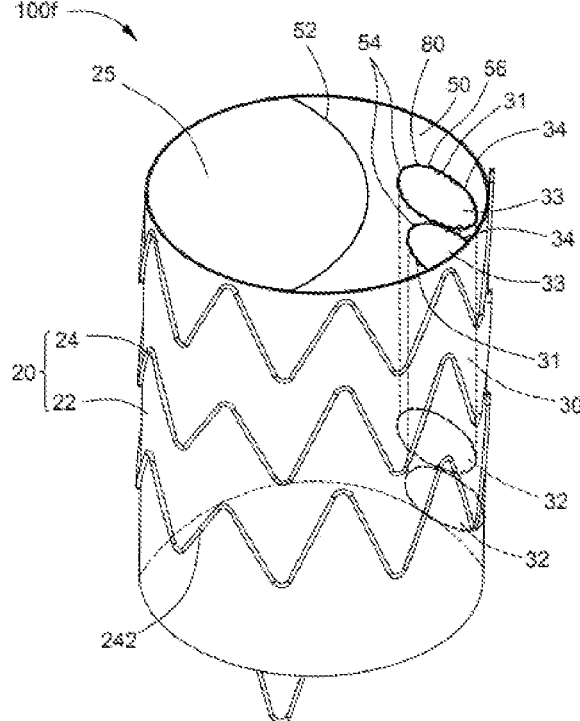
FIG. 18 is a schematic perspective view showing a structure of a vascular shunt stent according to a seventh embodiment of the present disclosure.

Reference is made to FIG. 18, wherein FIG. 18 is a schematic perspective view showing a structure of a vascular shunt stent 100f according to a seventh embodiment of the present disclosure. The structure of the vascular shunt stent 100f provided by the seventh embodiment of the present disclosure is similar to that of the second embodiment, with differences in that in the seventh embodiment, each of branch tubes 30 is provided with a marking element 80 at an edge of a first sub-opening 54, and the marking element 80 is a developing wire wound on an annular support member 56 continuously or discontinuously. Alternatively, the annular support member 56 is made of an alloy doped with a developing material, for example, the nickel-titanium metal wire is a tantalum-containing nickel-titanium alloy wire, with a diameter ranging from 0.10 mm to 0.40 mm.

In this embodiment, the annular support member 56 is a metal ring made of a shape-memory alloy, such as a nickel-titanium alloy ring structure. The metal ring is adapted to the shape of the periphery of the first sub-opening 54, and the marking element 80 is a developing wire wound on the metal ring continuously or discontinuously. Since the annular marking element 80 has a developing property and is an annular structure, the position of the annular marking element 80 can be observed using a developing device in the operation, that is, it can observe an annular marking element 80 along the circumference of the first sub-opening 54 instead of scattered developing points. Therefore, a branch vascular stent can be inserted into the first sub-opening 54 more conveniently and quickly. A material of the marking element includes, but is not limited to, gold, platinum, platinum tungsten, palladium, platinum-iridium, rhodium, tantalum, or alloys or composites of these metals.

In other embodiments, a developing material can be embedded in or attached to the outer surface of the annular support member 56 for at least one circle, for example, the developing metal wire 84 is embedded in the annular support member 56. Alternatively, the developing metal wire 84 is adhered to the outer surface of the annular support member 56 for at least one circle. Preferably, a tantalum wire is wound on the annular support member 56.

In other embodiments, the marking element 80 includes developing points continuously or discontinuously fixed on the first sealing film 50 at the periphery of the first sub-opening 54, and the developing point is fixed on the annular support member 56 by stitching, punching, thermal pressing, inserting or attaching, or is stitched on the first sealing film 50 where the annular support member 56 is positioned.

In other embodiments, the periphery of the main opening 52 is also provided with an annular marking element, and the annular marking element includes developing points continuously or discontinuously fixed on the first sealing film 50 at the periphery of the main opening 52.

Figure 19:
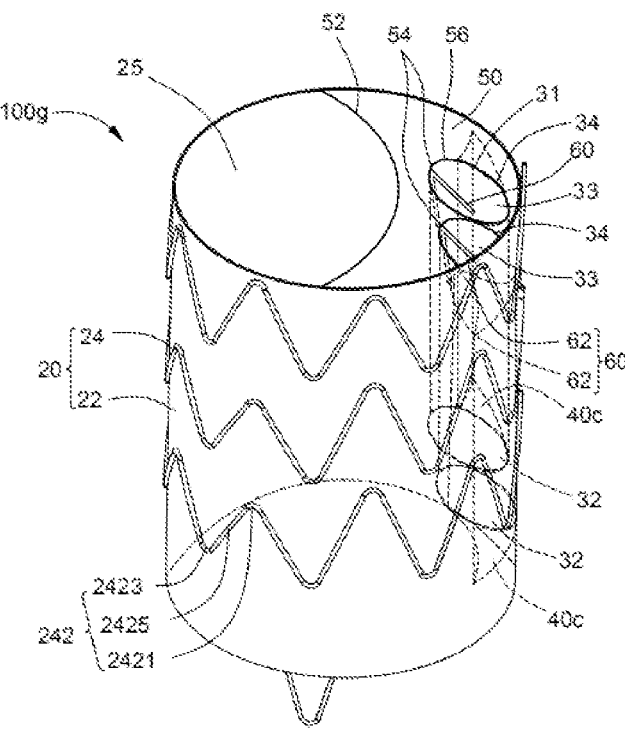
FIG. 19 is a schematic perspective view showing a structure of a vascular shunt stent according to an eighth embodiment of the present disclosure.

Reference is made to FIG. 19, wherein FIG. 19 is a schematic perspective view showing a structure of a vascular shunt stent 100g according to an eighth embodiment of the present disclosure. The structure of the vascular shunt stent 100g provided in the eighth embodiment of the present disclosure is similar to that of the fourth embodiment, with differences in that in the eighth embodiment, a proximal end of an annular support member 56 is arranged adjacent to an edge of one side of the first sealing film 50 away from the main membrane 22. At least one support member 60 is provided on the branch membrane 31 of each of the branch tubes 30. When the vascular shunt stent 100f is in a natural unfolded state, the support member 60 is configured to support the annular support member 56, to maintain the corresponding distal sub-opening 34 in an unfolded state, such that a branch tube stent can be conveniently inserted into the branch tube inner lumen 33 through the distal sub-opening 34. Specifically, the support member 60 has an inverted V shape, which includes two support rods 62 each having a first end, and the first ends of the two support rods 62 intersect, an intersection of the two support rods 62 is connected to the corresponding annular support member 56, and the two support rods 62 are respectively connected to the branch membrane 31. The support rods 62 can be fixed on the branch membrane 31 by stitching or thermal pressing. In this embodiment, the support rods 62 are fixed on an edge of the branch membrane 31 by stitching.

Figure 20:
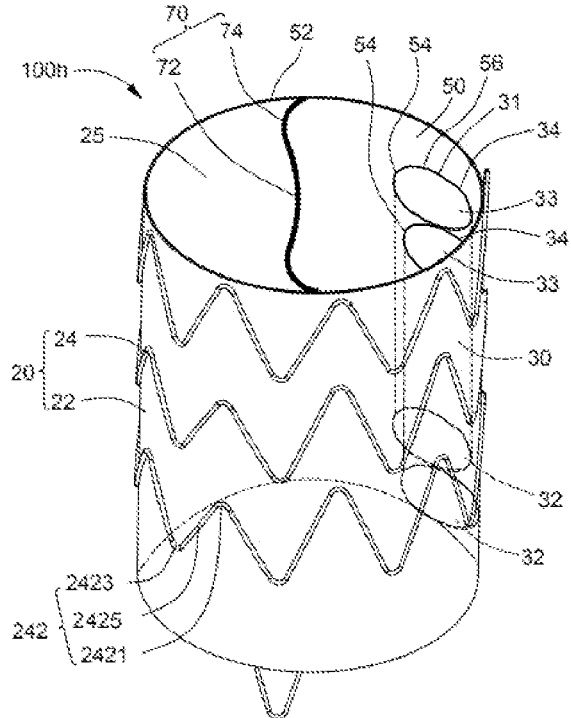
FIG. 20 is a schematic perspective view showing a structure of a vascular shunt stent according to a ninth embodiment of the present disclosure.

Reference is made to FIG. 20, wherein FIG. 20 is a schematic perspective view showing a structure of a vascular shunt stent 100h according to a ninth embodiment of the present disclosure. The structure of the vascular shunt stent 100h provided by the ninth embodiment of the present disclosure is similar to that of the second embodiment, with a difference in that in the ninth embodiment, a positioning member is provided at an edge of the main opening 52 of the first sealing film 50, and the positioning member is fixed on the first sealing film 50 at an edge of one side of the main opening 52 away from a side wall of the main body tube 20.

Specifically, the positioning member is a positioning rod 70 fixed on the first sealing film 50 at one side of the main opening 52 away from the side wall of the main body tube 20. The positioning rod 70 is elastic, and the positioning rod 70 is configured to position the first sealing film 50, that is, fix orientation of the first sealing film 50, increasing the supporting force of the edge of an opening of the first sealing film 50, and preventing one side of the first sealing film 50 away from the side wall of the main body tube 20 from collapsing. The positioning rod 70 is made of a shape memory alloy wire, preferably, a nickel-titanium wire.

The positioning rod 70 extends towards the center of the main body tube 20 from the edge of one side of the main opening 52 on the first sealing film 50 connected to the side wall of the main body tube 20. Two opposite ends of the positioning rod 70 are respectively connected to the side wall of the main body tube 20. Therefore, when the main body stent is inserted into the main opening 52 of the main body tube 20, the positioning rod 70 can be tightly attached to the outer surface of the main body stent, such that the first sealing film 50 is tightly attached to the outer surface of the main body stent to prevent endoleak, and also the main body stent can be conveniently inserted into the main opening 52 of the main body tube 20, the compatibility of the main body stent and the vascular shunt stent is increased, and the main body stent and the vascular shunt stent are engaged more stably.

In this embodiment, the positioning rod 70 is a wave-shaped structure formed by three curved rods connected to one another. The positioning rod 70 includes a first curved rod 72 in the middle, and two second curved rods 74 respectively connected to two opposite ends of the first curved rod 72, wherein the two second curved rods 74 have the same structure and are symmetrical with respect to a midpoint of the first curved rod 72. The two second curved rods 74 are smoothly connected with the first curved rod 72. The first curved rod 72 and the two second curved rods 74 are formed as a single piece, and the positioning rod 70 is formed by bending a shape memory alloy wire.

In other embodiments, the first curved rod 72 and the two second curved rods 74 may be formed separately, that is, the first curved rod 72 and the two second curved rods 74 are connected into a whole by mechanical compressing or welding.

As shown in FIG. 20, the middle of the first curved rod 72 is bent towards the main opening 52, and the middle of each of the second curved rods 74 is bent towards one side away from the main opening 52. The diameter of the positioning rod 70 is between 0.10 mm and 0.40 mm. In this embodiment, the diameter of the positioning rod 70 is between 0.20 mm and 0.30 mm. The positioning rod 70 can be fixed on the first sealing film 50 by stitching or thermal pressing. In this embodiment, the positioning rod 70 is fixed on the edge of the first sealing film 50 by stitching.

In other embodiments, the positioning rod 70 can be made of a shape memory alloy wire containing a developing material, to facilitate the insertion of the branch vascular stent into the main opening 52.

In other embodiments, a developing wire is wound on the positioning rod 70 continuously or discontinuously.

In other embodiments, a marking element is embedded in or attached to the positioning rod 70. For example, a developing metal wire is embedded in the positioning rod 70.

Figure 21:
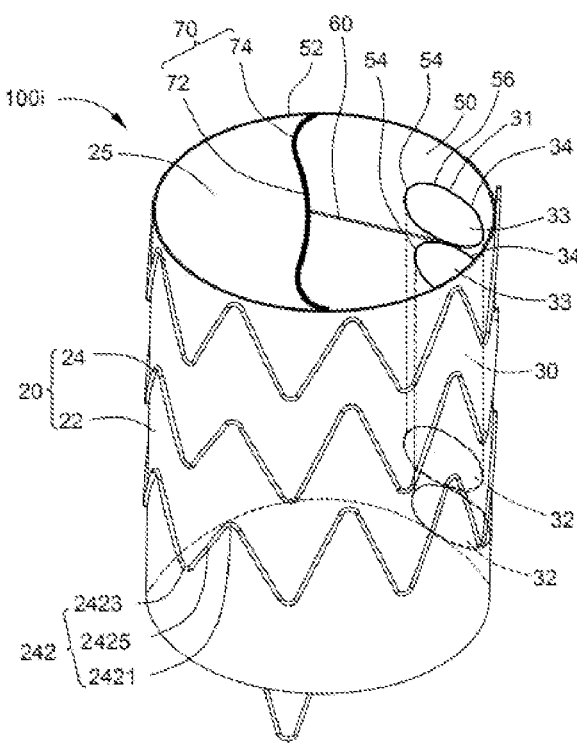
FIG. 21 is a schematic perspective view showing a structure of a vascular shunt stent according to a tenth embodiment of the present disclosure.

Reference is made to FIG. 21, wherein FIG. 21 is a schematic perspective view showing a structure of a vascular shunt stent 100i according to a tenth embodiment of the present disclosure. The structure of the vascular shunt stent 100i provided in the tenth embodiment of the present disclosure is similar to that of the ninth embodiment, with differences in that in the tenth embodiment, at least one support member 60 is provided on the first sealing film 50. At least one support member 60 is connected between the positioning rod 70 and the annular support member 56. At least one support member 60 is a support rod fixed to the first sealing film 50, one end of the support rod is connected to the positioning rod 70, and the other end of the support rod 60 is connected to the annular support member 56. The support rod 60 is made of a nickel-titanium wire with a wire diameter ranging from 0.10 mm to 0.40 mm, preferably, a wire diameter ranging from 0.20 mm to 0.30 mm.

In this embodiment, two first sub-openings 54 are provided in the first sealing film 50 which are tangent to each other. The main body tube inner lumen 25 of the main body tube 20 is provided with two branch tubes 30 therein. Distal ends of the two branch tubes 30 are respectively communicated with the two first sub-openings 54. The two first sub-openings 54 are positioned at one side away from the main opening 52, and the outer side surfaces of the two branch tubes 30 are attached to and in contact with an inner wall of the main body tube inner lumen 25. The support rod 60 is fixed to the first sealing film 50 and connected between the positioning rod 70 and the tangent point of the two first sub-openings 54. The first sealing film 50 is recessed towards the two first sub-openings 54, that is, the first sealing film 50 is inclined towards the two first sub-openings 54. Preferably, one end of the support rod 60 is fixed on the first curved rod 72 of the positioning rod 70, preferably, at a middle point of the first curved rod 72, and the other end of the support rod 60 is fixed at the tangential point of the first sub-openings 54.

Figure 22:
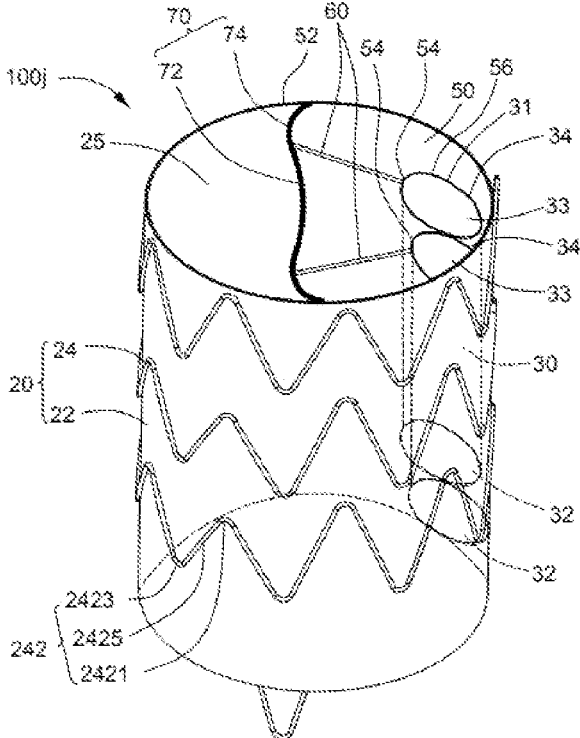
FIG. 22 is a schematic perspective view showing a structure of a vascular shunt stent according to an eleventh embodiment of the present disclosure.

Reference is made to FIG. 22, wherein FIG. 22 is a schematic perspective view showing a structure of a vascular shunt stent 100*j* according to an eleventh embodiment of the present disclosure. The structure of the vascular shunt stent 100*j* provided in the tenth embodiment of the present disclosure is similar to that of the ninth embodiment, with differences in that in the eleventh embodiment, two first sub-openings are provided in the first sealing film 50. Two support rods 60 are fixed on the first sealing film 50 separately, and the two support rods 60 are respectively connected between the edges of the two first sub-openings 54 and the positioning rod 70. Specifically, one end of each of the support rods 60 is fixed on a second curved rod 74 of the positioning rod 70, and the other end thereof is fixed on the annular support member 56 on the edge of the corresponding first sub-opening 54.

In this embodiment, the two support rods 60 each have an inverted truncated V shape.

In other embodiments, two support rods 60 can be parallel arranged and fixed on the first sealing film 50, and each of the support rods 60 is connected between the edge of the corresponding first sub-opening 54 and the positioning rod 70.

In other embodiments, three or more support rods 60 may be fixed on the first sealing film 50, and a part of the support rod 60 is connected to the annular support member 56 on the edge of one of the first sub-openings 54 and the positioning rod 70, and the other part of the support rod 60 is connected between the annular support member 56 on the edge of the other first sub-opening 54 and the positioning rod 70.

Figure 23:
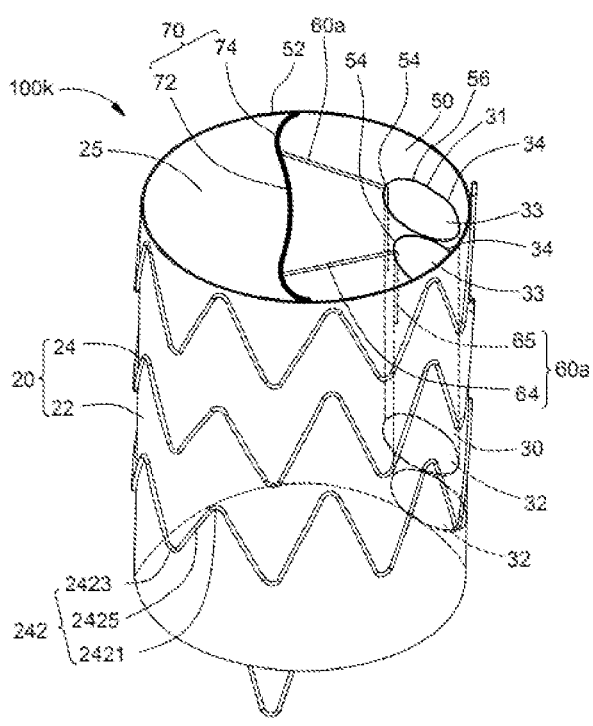
FIG. 23 is a schematic perspective view showing a structure of a vascular shunt stent according to a twelfth embodiment of the present disclosure.

Reference is made to FIG. 23, wherein FIG. 23 is a schematic perspective view showing a structure of a vascular shunt stent 100*k* according to a twelfth embodiment of the present disclosure. The structure of the vascular shunt stent 100*k* provided by the twelfth embodiment of the present disclosure is similar to that of the eleventh embodiment, with differences in that in the twelfth embodiment, as shown in FIG. 23, the support rod 60*a* includes a first rod body 64 and a second rod body 65 inclinedly connected to one end of the first rod body 64. An included angle between the first rod body 64 and the second rod body 65 ranges from 24° to 130°. The first rod body 64 of each of the support rods 60*a* is fixed on the first sealing film 50, and the second rod body 65 is fixed on the side wall of a corresponding branch tube 30, that is, the second rod body 65 is fixed on the branching membrane 31 of the corresponding branch tube 30. An intersection of the first rod body 64 and the second rod body 65 is positioned at an intersection of the first sealing film 50 and the side wall of the corresponding branch tube 30. The inclination angles of the first rod body 64 and the first sealing film 50 are the same, and the second rod body 65 extends along an axial direction of the corresponding branch membrane 31. One end of each of the first rod bodies 64 away from the corresponding second rod body 65 is fixed on the positioning rod 70. Preferably, the end of each of the first rod bodies 64 away from the corresponding second rod body 65 is fixed on the corresponding second curved rod 74.

In this embodiment, the first rod body 64 and the second rod body 65 are formed as one single piece, and the angle between the first rod body 64 and the second rod body 65 is formed by thermal pressing and bending. The first rod body 64 and the second rod body 65 are respectively fixed on the first sealing film 50 and the branch membrane 31 by stitching.

In this embodiment, the first rod body 64 of the support rod 60*a* is fixed on the first sealing film 50, and an end portion of the first rod body 64 away from the second rod body 65 is fixed on the positioning rod 70. The support rod 60*a* and the positioning rod 70 achieve a supporting function for the first sealing film 50. The second rod body 65 is fixed on the branch membrane 31, which can not only support the first sealing film 50 but also position the corresponding branch membrane 31. As a result, a radial supporting force of the branch tube 30 can be increased, such that the first sealing film 50 and the side wall of the main body tube 20 define a stable flared opening structure. Accordingly, the blood in the main body tube 20 and the branch tube 30 flows more smoothly, and the branch vascular stent can be conveniently inserted into the main opening 52 and the first sub-opening 54.

In other embodiments, the first sealing film 50 may be provided with only one support rod 60*a*. The first rod body 64 of the support rod 60*a* is fixed on the first sealing film 50, and an end portion of the first rod body 64 away from the second rod body 65 is fixed on the positioning rod 70, and the second rod body 65 is fixed on a tangent point of the two branch tubes 30.

In other embodiments, the first sealing film 50 may be provided with only one support rod 60*a*, only one first sub-opening 54 is provided in the first sealing film 50, and the first rod body 64 of the support rod 60*a* is fixed on the first sealing film 50, the second rod body 65 is fixed on the branch membrane 31 at the first sub-opening 54, an intersection of the first rod body 64 and the second rod body 65 is positioned at an intersection of the first sealing film 50 and the branch membrane 31, and one end of the first rod body 64 away from the second rod body 65 is connected to the positioning rod 70.

Figure 24:
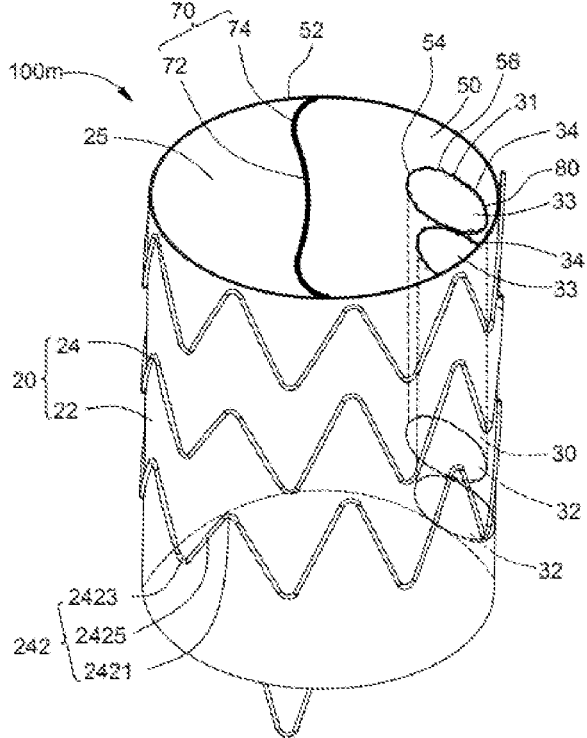
FIG. 24 is a schematic perspective view showing a structure of a vascular shunt stent according to a thirteenth embodiment of the present disclosure.

Reference is made to FIG. 24, wherein FIG. 24 is a schematic perspective view showing a structure of a vascular shunt stent 100*m* according to a thirteenth embodiment of the present disclosure. The structure of the vascular shunt stent 100*m* provided by the thirteenth embodiment of the present disclosure is similar to that of the ninth embodiment, with differences in that in the thirteenth embodiment, the branch tube 30 is provided with a marking element 80 at an edge of a first sub-opening 54, and the marking element 80 is a developing wire wound on the annular support member 56 continuously or discontinuously. Alternatively, the annular support member 56 is made of an alloy doped with a developing material, for example, the nickel-titanium metal wire is a tantalum-containing nickel-titanium alloy wire, and the diameter of the nickel-titanium alloy wire is ranged from 0.10 mm to 0.40 mm.

In this embodiment, the annular support member 56 is a metal ring made of a shape memory alloy, such as a nickel-titanium alloy annular structure. The metal ring is adapted to a shape of a periphery of the first sub-opening 54, and the marking element 80 is a developing wire wound continuously or discontinuously on the metal ring. Since the annular marking element 80 has a developing property and is an annular structure, the position of the annular marking element 80 can be observed through an imaging device in the operation, that is, it can observe an annular marking element 80 the circumference of the first sub-opening 54 instead of scattered developing points. Therefore, the branch vascular stent can be inserted into the first sub-opening 54 conveniently and quickly.

Figure 25:
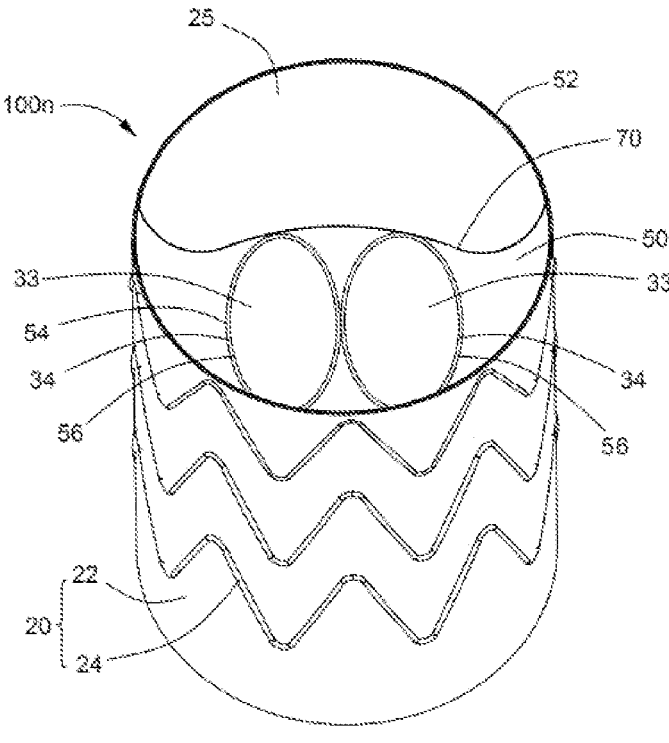
FIG. 25 is a schematic perspective view showing a structure of a vascular shunt stent according to a fourteenth embodiment of the present disclosure.

Reference is made to FIG. 25, wherein FIG. 25 is a schematic perspective view showing a structure of a vascular shunt stent 100$n$ according to a fourteenth embodiment of the present disclosure. The structure of the vascular shunt stent 100$n$ provided in the fourteenth embodiment of the present disclosure is similar to that of the ninth embodiment, with a difference in that in the fourteenth embodiment, an edge of an annular support member 56 is connected with a positioning rod 70. Specifically, one side of a first sub-opening 54 on a first sealing film 50 is located close to the positioning rod 70 or is tangent to the positioning rod 70, such that the annular support member 56 is arranged on the periphery of the first sub-opening 54 is connected with the positioning rod 70. Accordingly, the annular support member 56 stably expands the first sub-opening 54 to facilitate the insertion of the branch tube stent.

In this embodiment, two adjacent first sub-openings 54 are provided in the first sealing film 50, each of the first sub-openings 54 may be oval or circular, and the first sealing film 50 is provided with an oval or circular annular support member 56 on a periphery of each of the first sub-openings 54. A plane defined by each of the first sub-openings 54 is inclined to the axis of the main body tube 20. Specifically, an included angle between the plane defined by each of the first sub-openings 54 and the axis of the main body tube 20 is less than 90°. One side of the annular support member 56 on each of the first sub-openings 54 away from the main membrane 22 is connected to the positioning rod 70. The orientation of the first sealing film 50 can be further fixed by extension and support of the annular support member 56 on the first sealing film, such that the first sealing film 50 is prevented from collapsing into the main opening 52 and interfering with the implantation of the main body stent.

Figure 26:
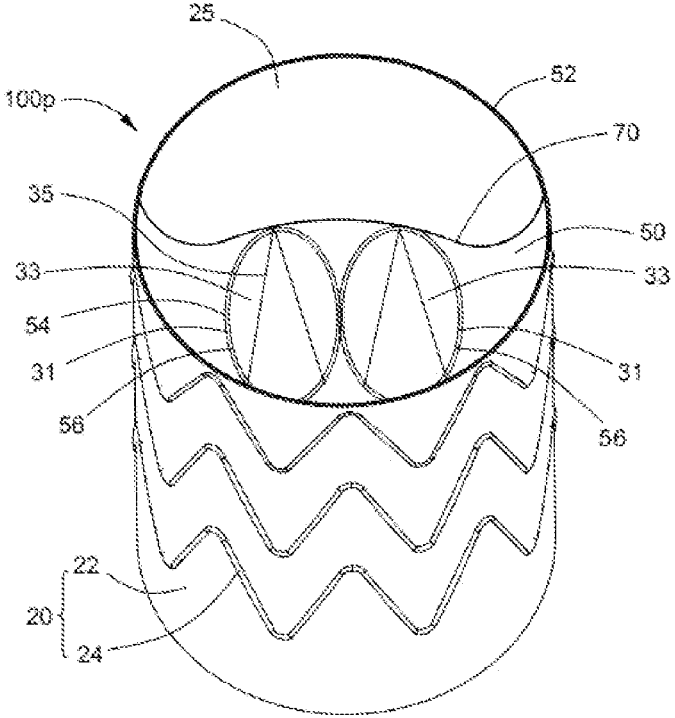
FIG. 26 is a schematic perspective view showing a structure of a vascular shunt stent according to a fifteenth embodiment of the present disclosure.

Reference is made to FIG. 26, wherein FIG. 26 is a schematic perspective view showing a structure of a vascular shunt stent 100$p$ according to a fifteenth embodiment of the present disclosure. The structure of the vascular shunt stent 100$p$ provided by the fifteenth embodiment of the present disclosure is similar to that of the fourteenth embodiment, with a difference in that in the fifteenth embodiment, a distal end of the annular support member 56 and a distal end of a wave-shaped support member 35 are both connected to the positioning rod 70. Specifically, a wave-shaped support member 35 is fixed on each of branch membranes 31, the distal end of the wave-shaped support member 35 at the most distal end of the branch membrane 31 is connected to the distal end of the corresponding annular support member 56, and a connection of the wave-shaped support member 35 and the annular support member 56 is connected with the positioning rod 70, such that a first sub-opening 54 can be more stably expanded, which facilitate the inserting of a branch tube stent.

In other embodiments, as shown in FIG. 27, the wave-shaped support member 35 is of a structure in which high waves and low waves are arranged alternately, the wave-shaped support member 35 includes a high-wave support rod 351 and a low-wave support rod 352, and a distal end of the high-wave support rod 351 is adjacent to a distal end of the annular support member 56. Preferably, the distal end of the high-wave support rod 351 is connected with the distal end of the annular support member 56, to improve the overall supporting stability of the first sealing film 50 and the branch membrane 31.

In other embodiments, as shown in FIG. 28, a proximal end 3512 of the high-wave support rod 351 is parallel to the axis of the main body tube 20, and an included angle between a distal end 3511 of the high-wave support rod and the axis of the main body tube 20 is greater than 0° and less than 90°. Preferably, the distal end 3511 of the high-wave support rod is parallel to a plane where the annular support member 56 is positioned, that is, preferably, an included angle between the distal end 3511 of the high-wave support rod and the axis of the main body tube 20 is greater than 5° and less than 80°. More preferably, the included angle is greater than 30° and less than 60°. Using the support of both the high-wave support rod 3512 at the first sealing film 50 and the distal end of the annular support member 56, the orientation of the first sealing film 50 can be fixed, to prevent the first sealing film 50 from collapsing and sagging. Meanwhile, the design is simpler, such that the overall amount of the used metal material of the vascular shunt stent is reduced, and the vascular shunt stent can be implanted through a deliverer sheath with a smaller diameter.

Reference is made to FIG. 29, wherein FIG. 29 is a schematic perspective view showing a structure of a vascular shunt stent 100$s$ according to a sixteenth embodiment of the present disclosure. The structure of the vascular shunt stent 100$s$ provided in the sixteenth embodiment of the present disclosure is similar to that of the fifteenth embodiment, with a difference in that in the sixteenth embodiment, a periphery of the first sub-opening 54 and/or a periphery of the main opening 52 are/is provided with a marking element 80, and the marking element 80 is a developing wire continuously or discontinuously wound on the annular support member 56. Alternatively, the annular support member 56 is made of an alloy doped with a developing material, for example, the nickel-titanium metal wire is a tantalum-containing nickel-titanium alloy wire, and the diameter of the nickel-titanium alloy wire is ranged from 0.10 mm to 0.40 mm.

In this embodiment, the annular support member 56 is a metal ring made of a memory alloy, such as a nickel-titanium alloy annular structure, the metal ring is adapted to the shape of the periphery of the first sub-opening 54, and the marking element 80 is a developing wire wound continuously or discontinuously on the metal ring. Since the annular marking element 80 has a developing property and is an annular structure, the position of the annular marking element 80 can be observed through an imaging device in the operation, that is, it can observe an annular marking element 80 along a circumference of the first sub-opening 54 instead of scattered imaging points. Accordingly, a branch vascular stent can be inserted into the first sub-opening 54 conveniently and quickly.

An included angle between a plane where the annular support member 56 surrounding the first sub-opening 54 or the second sub-opening is positioned and the axis of the main body tube 20 is greater than 0° and less than 90° preferably, greater than 5° and less than 80°. More preferably, the included angle is greater than 45° and less than 60°. The annular support members 56 arranged at two ends of the branch tube are not perpendicular to the axis of the main body tube 20. The annular support member 56 on the vascular shunt stent 100$s$ under compressing and crimping may be severely deformed when being subjected to a pressure perpendicular to the axis of the main body tube, which results in a shape not being maintained well. However, the first sub-opening 54 and the annular support member 56 surrounding it are not perpendicular to the axis of the main body tube 20, preventing the branch stent from being crimped by a perpendicular radial force. As a result, the shapes of the sub-opening 54 and the annular support members 56 can be well maintained, and the branch stent can be conveniently implanted.

It should be noted that specific technical solutions in the above embodiments are applicable to each other without departing from the principle of the embodiments of the present disclosure, which will not be repeated here.

The above are implementations of the embodiments of the present disclosure. It should be noted that those ordinarily skilled in the art can make several improvements and modifications without departing from the principle of the embodiments of the present disclosure. These improvements and modifications are regarded as within the protection scope of the present disclosure.

What is claimed is:

1. A vascular shunt stent, comprising a main body tube and at least one branch tube axially inserted into the main body tube, wherein the main body tube comprises a tubular main membrane, at least one of the at least one branch tube comprises a tubular branch membrane, the branch membrane is accommodated in an inner lumen of the main membrane, a first sealing film is connected to a distal end of the main membrane and a distal end of the branch membrane, the first sealing film covers partially the distal end of the main membrane with a main opening being defined by an edge of the first sealing film and a distal edge of the main membrane, the first sealing film defines at least one first sub-opening at a central portion thereof corresponding to the distal end of the branch membrane, the first sealing film is in sealed connection with the distal end of the branch membrane at a periphery of the first sub-opening, the first sealing film extends inclinedly relative to an axial axis of the main body tube, and a plane defined by the first sub-opening and a plane defined by the main opening are non-parallel or non-coplanar;

wherein a proximal end of the branch membrane is provided with a second sub-opening;

wherein a leakage preventing member is provided between the main membrane and the branch membrane at a periphery of the second sub-opening; and wherein the leakage preventing member comprises leakage preventing frames disposed on two opposite sides of the branch membrane, and the leakage preventing frames are configured to seal a gap between a proximal end of the branch membrane and the main membrane.

2. The vascular shunt stent according to claim 1, wherein the plane defined by the main opening is perpendicular to the axial axis of the main body tube.

3. The vascular shunt stent according to claim 2, wherein an included angle between the plane defined by the first sub-opening and the axial axis of the main body tube is less than 90°.

4. The vascular shunt stent according to claim 3, wherein the included angle between the plane defined by the first sub-opening and the axial axis of the main body tube is greater than 5° and less than 80°.

5. The vascular shunt stent according to claim 1, wherein the plane defined by the first sub-opening is parallel to a plane defined by the second sub-opening.

6. The vascular shunt stent according to claim 5, wherein each of the first sub-opening and the second sub-opening is provided with an annular support member there around.

7. The vascular shunt stent according to claim 6, wherein the annular support member at the first sub-opening is a ring attached to the periphery of the first sub-opening.

8. The vascular shunt stent according to claim 7, wherein a surface of the branch membrane is provided with at least one wave-shaped support member, and a distal end of at least one of the at least one wave-shaped support member is adjacent to the annular support member at the first sub-opening.

9. The vascular shunt stent according to claim 8, wherein the wave-shaped support member is of a structure in which low waves and high waves are arranged at intervals, the wave-shaped support member comprises a high-wave support rod and a low-wave support rod, a proximal end of the high-wave support rod is parallel to the axial axis of the main body tube, and an included angle between a distal end of the high-wave support rod and the axial axis of the main body tube is greater than 0° and less than 90°.

10. The vascular shunt stent according to claim 9, wherein an edge of the distal end of the high-wave support rod is adjacent to an edge of the distal end of the annular support member at the first sub-opening.

11. The vascular shunt stent according to claim 9, wherein an edge of the main opening is provided with a positioning member, and the positioning member is fixed on the first sealing film at the edge of one side of the main opening away from a side wall of the main body tube.

12. The vascular shunt stent according to claim 11, wherein the edge of the annular support member at the first sub-opening is connected with the positioning member.

13. The vascular shunt stent according to claim 11, wherein the distal end of the annular support member and the distal end of the wave-shaped support member are connected with the positioning member.

14. The vascular shunt stent according to claim 1, wherein each leakage preventing frame comprises a distal end surface attached to the first sealing film, a proximal end surface facing away from the distal end surface, a first attaching surface attached to the branch membrane, a second attaching surface attached to the main membrane and a sealing surface connected to the distal end surface, the proximal end surface, the first attaching surface and the second attaching surface, at least the proximal end surface is provided with a second sealing film and the sealing surface is provided with a third sealing film, the distal end surface, and the first sealing film share a membrane, the first attaching surface and the branch membrane share a membrane, and the second attaching surface and the main membrane share a membrane.

15. The vascular shunt stent according to claim 14, wherein an inner lumen of each leakage preventing membrane frame is filled with an expandable material, or the inner lumen of each leakage preventing membrane frame is provided with a villi structure.

16. A vascular stent, comprising a main body stent and a branch tube stent, wherein the vascular stent further comprises the vascular shunt stent according to claim 1, wherein one end of the main body stent is inserted into the main body tube of the vascular shunt stent through the main opening on the first sealing film, and one end of the branch tube stent is inserted into the branch tube through the first sub-opening on the first sealing film.

* * * * *